(12) United States Patent
Nyberg et al.

(10) Patent No.: US 9,579,024 B2
(45) Date of Patent: Feb. 28, 2017

(54) SYSTEM AND METHOD FOR MEASURING BIOLOGICAL FLUID BIOMARKERS

(71) Applicant: CoreSyte, Inc., Great Falls, VA (US)

(72) Inventors: Sten Adam Nyberg, Dayton, OH (US); Dalton Pont, Sterling, VA (US)

(73) Assignee: CoreSyte, Inc., Great Falls, VA (US)

( * ) Notice: Subject to any disclaimer, the term of this patent is extended or adjusted under 35 U.S.C. 154(b) by 0 days.

(21) Appl. No.: 15/177,686

(22) Filed: Jun. 9, 2016

(65) Prior Publication Data

US 2016/0331235 A1 Nov. 17, 2016

Related U.S. Application Data

(63) Continuation-in-part of application No. 15/014,526, filed on Feb. 3, 2016.
(Continued)

(51) Int. Cl.
| | |
|---|---|
| A61B 5/05 | (2006.01) |
| A61B 5/00 | (2006.01) |
| A61B 5/145 | (2006.01) |
| A61B 5/1477 | (2006.01) |
| A61B 5/1473 | (2006.01) |
| A61B 10/00 | (2006.01) |

(52) U.S. Cl.
CPC ......... *A61B 5/0022* (2013.01); *A61B 5/0024* (2013.01); *A61B 5/1473* (2013.01); *A61B 5/1477* (2013.01); *A61B 5/14517* (2013.01); *A61B 5/14546* (2013.01); *A61B 5/4266* (2013.01); *A61B 5/6833* (2013.01); *A61B 10/0064* (2013.01); *A61B 5/0017* (2013.01); *A61B 2562/164* (2013.01)

(58) Field of Classification Search
CPC ............. A61B 5/4266; A61B 10/0064; A61B 2562/168; A61B 2562/0295; A61B 5/6833; A61B 5/6832; A61B 2562/164; A61B 5/150969; A61B 10/0096; A61B 5/14517; B01L 2300/023; B01L 2300/0645; B01L 2300/0803; B01L 2400/0406; G01N 27/3273; G01N 27/3271; G01N 27/3272
See application file for complete search history.

(56) References Cited

U.S. PATENT DOCUMENTS

| | | |
|---|---|---|
| 5,310,469 A | 5/1994 | Cunningham et al. |
| 5,718,816 A | 2/1998 | Savage et al. |

(Continued)

FOREIGN PATENT DOCUMENTS

| | | | |
|---|---|---|---|
| WO | 8700286 A1 | | 1/1987 |
| WO | WO2010045247 | * | 4/2010 |

(Continued)

OTHER PUBLICATIONS

U.S. Appl. No. 62/003,707, filed May 28, 2015, University of Cincinnati.
(Continued)

*Primary Examiner* — Navin Natnithithadha
*Assistant Examiner* — Eric Messersmith
(74) *Attorney, Agent, or Firm* — Triangle Patents, PLLC

(57) ABSTRACT

Systems and methods of analyzing biological fluid biomarkers, calculating biomarker data, transmitting data to a transceiver device, and storing the data and/or analytics in a database and/or on at least one remote computer server.

20 Claims, 54 Drawing Sheets

Related U.S. Application Data

(60) Provisional application No. 62/130,039, filed on Mar. 9, 2015.

(56) References Cited

U.S. PATENT DOCUMENTS

| | | | |
|---|---|---|---|
| 6,198,953 | B1 | 3/2001 | Webster et al. |
| 7,575,549 | B2 | 8/2009 | Miller |
| 8,388,534 | B2 | 3/2013 | Jang et al. |
| 2006/0253011 | A1 | 11/2006 | Edmonson et al. |
| 2007/0096604 | A1 | 5/2007 | Edmonson et al. |
| 2008/0039700 | A1 | 2/2008 | Drinan et al. |
| 2010/0176006 | A1 | 7/2010 | Bickford et al. |
| 2014/0330096 | A1 | 11/2014 | Brunswick |
| 2014/0350432 | A1 | 11/2014 | Khalfallah et al. |
| 2015/0019135 | A1 | 1/2015 | Kacyvenski et al. |
| 2015/0057515 | A1* | 2/2015 | Hagen ............... A61B 10/0064 600/346 |
| 2015/0112164 | A1 | 4/2015 | Heikenfeld et al. |
| 2015/0112165 | A1 | 4/2015 | Heikenfeld |

FOREIGN PATENT DOCUMENTS

| | | |
|---|---|---|
| WO | 2013152087 A2 | 10/2013 |
| WO | 2014197822 A2 | 12/2014 |
| WO | 2015058055 A1 | 4/2015 |
| WO | 2015058064 A1 | 4/2015 |
| WO | 2015184084 | 12/2015 |
| WO | 2015184084 A2 | 12/2015 |

OTHER PUBLICATIONS

Liu, et al. "Implementation of a microfluidic conductivity sensor—A potential sweat electrolyte sensing system for dehydration detection," in Conf Proc IEEE Eng Med Biol Soc, 2014:1678-81, 5 pgs.

Jason Heikenfeld, "Let Them See You Sweat", IEEE Spectrum, Nov. 2014, p. 46.

Daniel P. Rose, M. Ratterman, Daniel K. Griffin, Linlin Hou, Nancy Kelley-Loughnane, Rajesh R. Naik, Joshua A. Hagen, I. Papautsky, Jason Heikenfeld, Adhesive RFID Sensor Patch for Monitoring of Sweat Electrolytes, IEEE Transactions on Biomedical Engineering, Paper ID # TBME-00773-2014-R1.

Jason C. Heikenfeld, U.S. Appl. No. 62/023,233, Provisional Patent Application; Entire Document.

University of Cincinnati, U.S. Appl. No. 62/003,675, Provisional Patent Application; Entire Document.

University of Cincinnati, U.S. Appl. No. 62/003,707, Provisional Patent Application; Entire Document.

University of Cincinnati, U.S. Appl. No. 61/620,069, Provisional Patent Application; Entire Document.

Jason C. Heikenfeld, U.S. Appl. No. 61/892,859, Provisional Patent Application; Entire Document.

* cited by examiner

PRIOR ART FIG. 1

| | Current Detection & Treatment | | | |
|---|---|---|---|---|
| Micro Biomarker Anomaly | Symptoms | Degraded Performance | Injury | |
| Na, K, CL, Ca | | | Metabolites | |
| Lactate, Glucose Creatinine, Acids | | | Small Molecules | |
| Cortisol, IL, NeuroP | | | Proteins | |
| | | | Electrolytes | |

| Low Electrolytes | Cramps, Headaches | Slower, Lock Up | Tissue/Tendon Tear |
|---|---|---|---|
| Metabolite Imbalance | Nausea, Vomit, Disorient | Cognitive Errors | TBI, Neural Damage |
| Small Molecule Build Up | Stiffness, Fatigue | Shut Down | Organ Damage |
| Signal Protein Presence | Fever, Fatigue | Incapacitated | Organ Failure |

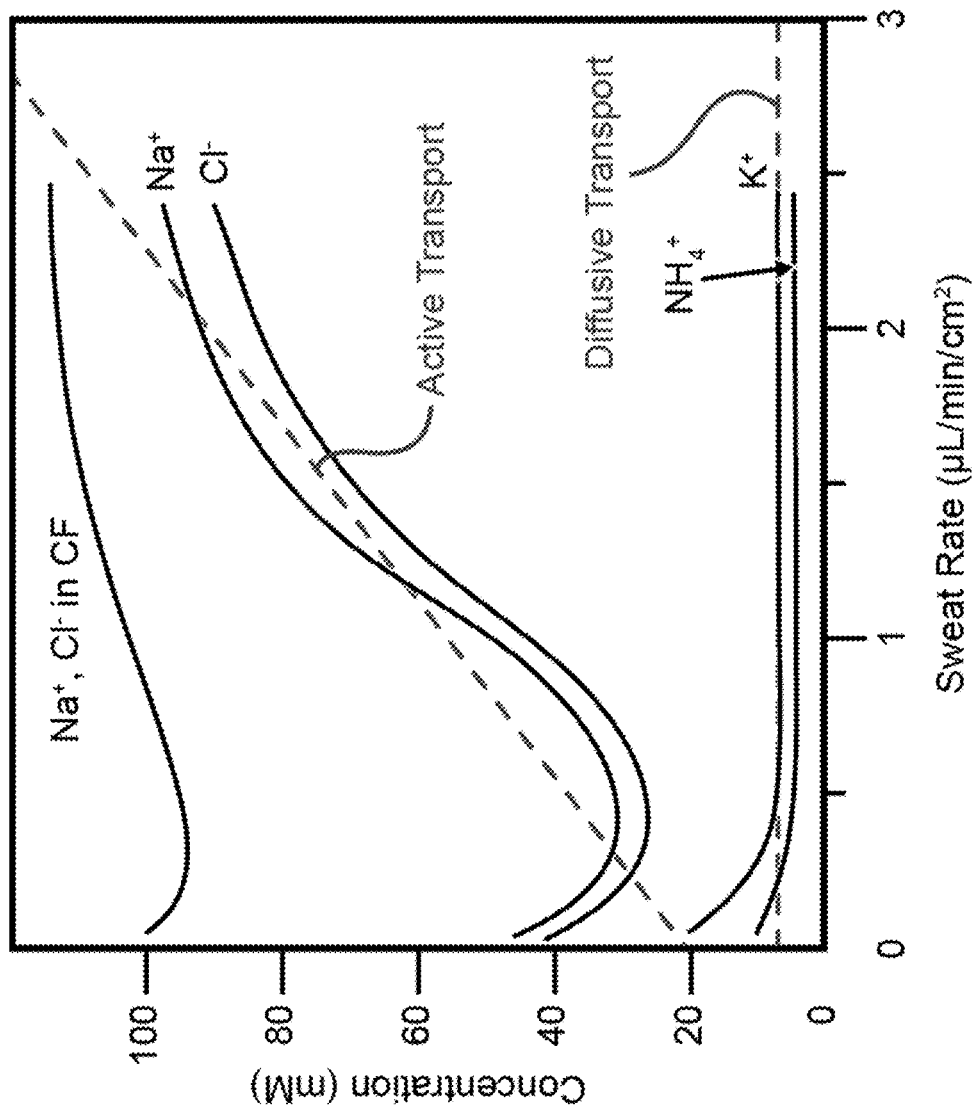
PRIOR ART FIG. 2

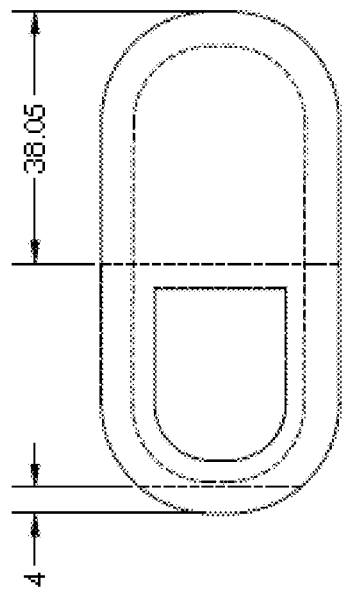
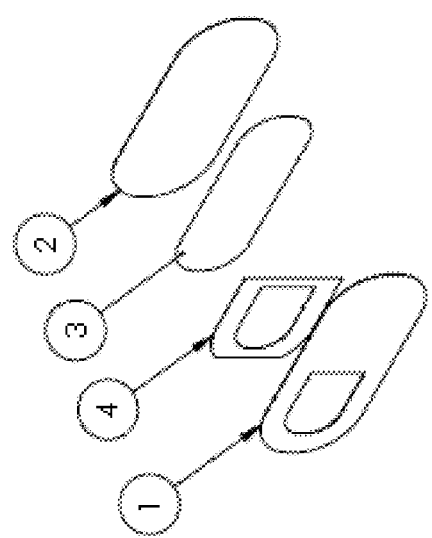
| ITEM NO. | PART NUMBER | DESCRIPTION | QTY. |
|---|---|---|---|
| 1 | 3M 9917 | Double Sided Adhesive | 1 |
| 2 | 3M 9926T | Woven Top Adhesive | 1 |
| 3 | Key Electronics PCB | Polyimide Flex PCB | 1 |
| 4 | GE Whatman 1001 | Grade 1 Filter Paper | 1 |
FIG. 3

Basic Ratio for Sweat Flow Rate (SFR)

| K (mV : mM) | Na (mV : mM) | Ratio (Na/K) | SFR (uL/min/cm$^2$) |
|---|---|---|---|
| 25 : 5 | 100 : 20 | 4 | 0.0 |
| 25 : 5 | 150 : 30 | 6 | 0.5 |
| 25 : 5 | 250 : 50 | 10 | 1.0 |
| 25 : 5 | 400 : 80 | 16 | 1.5 |
| 25 : 5 | 450 : 90 | 18 | 2.0 |
| 25 : 5 | 500 : 100 | 20 | 2.5 |
| 25 : 5 | 550 : 110 | 22 | 3.0 |

FIG. 11A

Body Surface Area (BSA) Calcs

| | |
|---|---|
| DuBois and DuBois[1] | BSA (m2) = 0.007184 × Height(cm)0.725 × Weight(kg)0.425 |
| Gehan and George[2] | BSA (m2) = 0.0235 × Height(cm)0.42246 × Weight(kg)0.51456 |
| Haycock[3] | BSA (m2) = 0.024265 × Height(cm)0.3964 × Weight(kg)0.5378 |
| Mosteller[4] (CoreSyte Uses) | BSA (m2) = SQR RT ( [Height(cm) × Weight(kg) ]/ 3600 ) |

Sweat Loss & Body Mass Loss Calcs

| | | | |
|---|---|---|---|
| Sweat Loss 1 | SFR1 × (Use Ratio) | BSA × (Use Calc) (User Ht Wt Inputs) | Dur (From Session Time) |
| Sweat Loss 2 | SFR2 × (KSI table, User Wt Input, Phone Temp) (Sweat Stds Table) | | Dur (Sess Time) |
| Sweat Mass | Convert SL1 Vol (L) to Mass (Kg) | | |
| % Body Mass Loss | Sweat Mass/User Wt | | |
| Sweat Loss Ratio (SLR) | SL1/SL2 (Sweat More/Less Than Norm) | | |

| Work Level | Level 1 | | Level 2 | | Level 3 | |
|---|---|---|---|---|---|---|
| Zone | Zone 1 | Zone 2 | Zone 3 | Zone 4 | Zone 5 | Zone 6 |
| SFR | 0.5 | 1.0 | 1.5 | 2.0 | 2.5 | 3.0 |
| mV Ratio | 0-6 | 7-10 | 11-16 | 17-18 | 18-20 | 21+ |
| Na Loss | 40 | 50 | 70 | 80 | | |
| K Loss | 4 | 5 | 7 | 8 | | |
| Typ Wt | Under 120 | 120-220 | 220-260 | 260+ (SFR Affected by HR & Temp) | | |
| Elite | | | NCAA Players (Source NIH/NCBI) | | | |
| | | | | NFL Players (Source NIH/NCBI) | | |
| | | | | NHL Players (Source NIH/NCBI) | | |
| | | | | | NBA Players | |

UT & GSSI Publication

Table 2. Sweating Rate and Sweat Sodium Concentration

| Variable | Mean±SE | CV (%) |
|---|---|---|
| Sweating Rate (L·hr⁻¹) | 1.4±0.1 | 30.8 |
| Sweating Rate (ml·kg⁻¹·hr⁻¹) | 19.4±1.7 | 28.5 |
| Sweat [Na] - Arm (mEq·L⁻¹) | 39.8±2.0 | 42.6 |
| Sweat [Na] - Back (mEq·L⁻¹) | 47.2±2.3 | 41.2 |
| Mean Sweat [Na] - Arm,Back (mEq·L⁻¹) | 43.4±2.1 | 40.0 |
| Na Loss - Arm (mEq·hr⁻¹) | 56.5±3.9 | 58.7 |
| Na Loss - Back (mEq·hr⁻¹) | 66.8±4.5 | 56.2 |
| Mean Na Loss - Arm,Back (mEq·hr⁻¹) dNa/dT | 61.6±4.1 | 56.0 |
| Na Loss - Arm (mEq·hr⁻¹·kg⁻¹) | 0.8±0.1 | 57.5 |
| Na Loss - Back (mEq·hr⁻¹·kg⁻¹) | 0.8±0.1 | 54.5 |
| Mean Na Loss - Arm,Back (mEq·hr⁻¹·kg⁻¹) dNa/dW | 0.8±0.1 | 54.0 |

FIG. 11C

Estimated sodium loss during moderate intensity exercise. (Na loss is calculated as whole body sweat rate x mean sweat [Na]).

FIG. 11D

Sweat Stds for Typical User (KSI, ACSM, GSSI, Runners World)

| BSA | Temp (°F) | Sweat (oz/min) | SFR2 |
|---|---|---|---|
| 100 lbs | 50 | 0.3 | 0.61045569 Zone 1 |
| Ave Ht 63" | 60 | 0.3 | |
| Ave BSA (m²) | 70 | 0.3 | |
| 1.45335018 | 80 | 0.4 | |
| | 90 | 0.4 | |
| | 100 | 0.5 | 0.95638858 Zone 2 |
| 120 lbs | 50 | 0.4 | |
| Ave Ht 68" | 60 | 0.4 | |
| Ave BSA (m²) | 70 | 0.4 | |
| 1.65707416 | 80 | 0.4 | |
| | 90 | 0.5 | |
| | 100 | 0.6 | 0.99943278 |
| 140 lbs | 50 | 0.4 | |
| Ave Ht 70" | 60 | 0.4 | |
| Ave BSA (m²) | 70 | 0.5 | |
| 1.833128673 | 80 | 0.5 | |
| | 90 | 0.6 | |
| | 100 | 0.7 | 1.04863311 |
| 160 lbs | 50 | 0.5 | |
| Ave Ht 73" | 60 | 0.5 | |
| Ave BSA (m²) | 70 | 0.5 | |
| 1.092893964 | 80 | 0.6 | |
| | 90 | 0.7 | |
| | 100 | 0.7 | 1.09812224 |
| 180 lbs | 50 | 0.5 | |
| Ave Ht 75" | 60 | 0.6 | |
| Ave BSA (m²) | 70 | 0.6 | |
| 2.135530278 | 80 | 0.7 | |
| | 90 | 0.7 | |
| | 100 | 0.8 | 1.16329978 |
| 200 lbs | 50 | 0.6 | |
| Ave Ht 76" | 60 | 0.6 | |
| Ave BSA (m²) | 70 | 0.7 | |
| 2.260032813 | 80 | 0.7 | |
| | 90 | 0.8 | |
| | 100 | 0.9 | 1.21696553 |
| 220 lbs | 50 | 0.7 | |
| Ave Ht 77" | 60 | 0.7 | |
| Ave BSA (m²) | 70 | 0.7 | |
| 2.38071595 | 80 | 0.8 | |
| | 90 | 0.9 | |
| | 100 | 1.0 | 1.26711883 Zone 3 |
| 240 lbs | 50 | 0.7 | |
| Ave Ht 77" | 60 | 0.8 | |
| Ave BSA (m²) | 70 | 0.8 | |
| 2.482067957 | 80 | 0.9 | |
| | 90 | 1.0 | |
| | 100 | 1.2 | 1.42095279 |
| 260+ lbs | 50 | 0.8 | |
| Ave Ht 77" | 60 | 0.8 | |
| Ave BSA (m²) | 70 | 1.0 | Zone 4 |
| 2.579440686 | 80 | 1.4 | |
| | 90 | 1.8 | |
| | 100 | 2.2 | 2.52287251 |

Normal Sweat Rate Range

FIG. 12A

| Basic Concentration Conversions | | | | | |
|---|---|---|---|---|---|
| K (mV) | K (mM) | Na (mV) | Na (mM) | | |
| 0 | 0 | 0 | 0 | Specified Range | |
| 17 | 40 | 57 | 110 | Specified Range | |
| 30 | 14 | 50 | 17 | Test Range | |
| 80 | 135 | 130 | 171 | Test Range | |
| K Ratio | 2.4 | Na Ratio | 1.9 | mM/mV | |

FIG. 12C

Basic mV Ratios (Same as mM Ratios)

| Na/K(mV/ | SFR1 | | |
|---|---|---|---|
| 1 | | | |
| 2 | | | |
| 3 | | | |
| 4 | 0.00 | | |
| 5 | 0.25 | | Zone 1 |
| 6 | 0.50 | 0.125 | |
| 7 | 0.63 | | |
| 8 | 0.75 | | Zone 2 |
| 9 | 0.88 | | |
| 10 | 1.00 | 0.083 | |
| 11 | 1.08 | | |
| 12 | 1.17 | | |
| 13 | 1.25 | | Zone 3 |
| 14 | 1.33 | | |
| 15 | 1.42 | | |
| 16 | 1.50 | 0.250 | |
| 17 | 1.75 | | |
| 18 | 2.00 | | Zone 4 |
| 19 | 2.25 | | |
| 20 | 2.50 | | |
| 21 | 2.75 | | Zone 5 |
| 22 | 3.00 | | |
| 23 | 3.25 | | Zone 6 |
| 24 | 3.50 | | |
| 25 | | | |

FIG. 13A

| Biomarker | [K] (mM) | [Na] (mM) | %BML |
|---|---|---|---|
| Max Low | 0 | 20 | 0 |
| Max High | 20 | 110 | 4 |
| | K Loss (mg) | Na Loss (mg) | BML% |
| Green 1 | 0.0 | 0.0 | 0.0 |
| Green 2 | 50.0 | 149.0 | 1.5 |
| Yellow 1 | 200.0 | 150.0 | 1.6 |
| Yellow 2 | 299.0 | 199.0 | 2.5 |
| Red Hi | 300.0 | 200.0 | 2.6 |

| | |
|---|---|
| Green 1 | 5 |
| Green 2 | 4 |
| Yellow 1 | 3 |
| Yellow 2 | 2 |
| Red Hi | 1 |

FIG. 13B

| Intense Selection | User Input at Session Start | | From Phone | | From Sensor |
|---|---|---|---|---|---|
| | User Wt Input | | Atm Temp | | Na/K Ratio |
| User Input Low (1) | wt<140 (1) | | T°F<80 (1) | | <10 (1) |
| User Input Med (2) | wt<200>140 (2) | | T°F<90>80 (2) | | 10-18 (2) |
| User Input High (3) | wt>200 (3) | | T°F>90 (3) | | >18 (3) |
| | | | Not Skin T | | |
| | These values should be adjustable in the CLOUD | | | | |
| Level 1 | Add Up Scores from Inputs Above Intens+Wt+Temp+Ratio | | <4 | | |
| Level 2 | | | 4-10 | | |
| Level 3 | | | >10 | | |

FIG. 27

FIG. 28
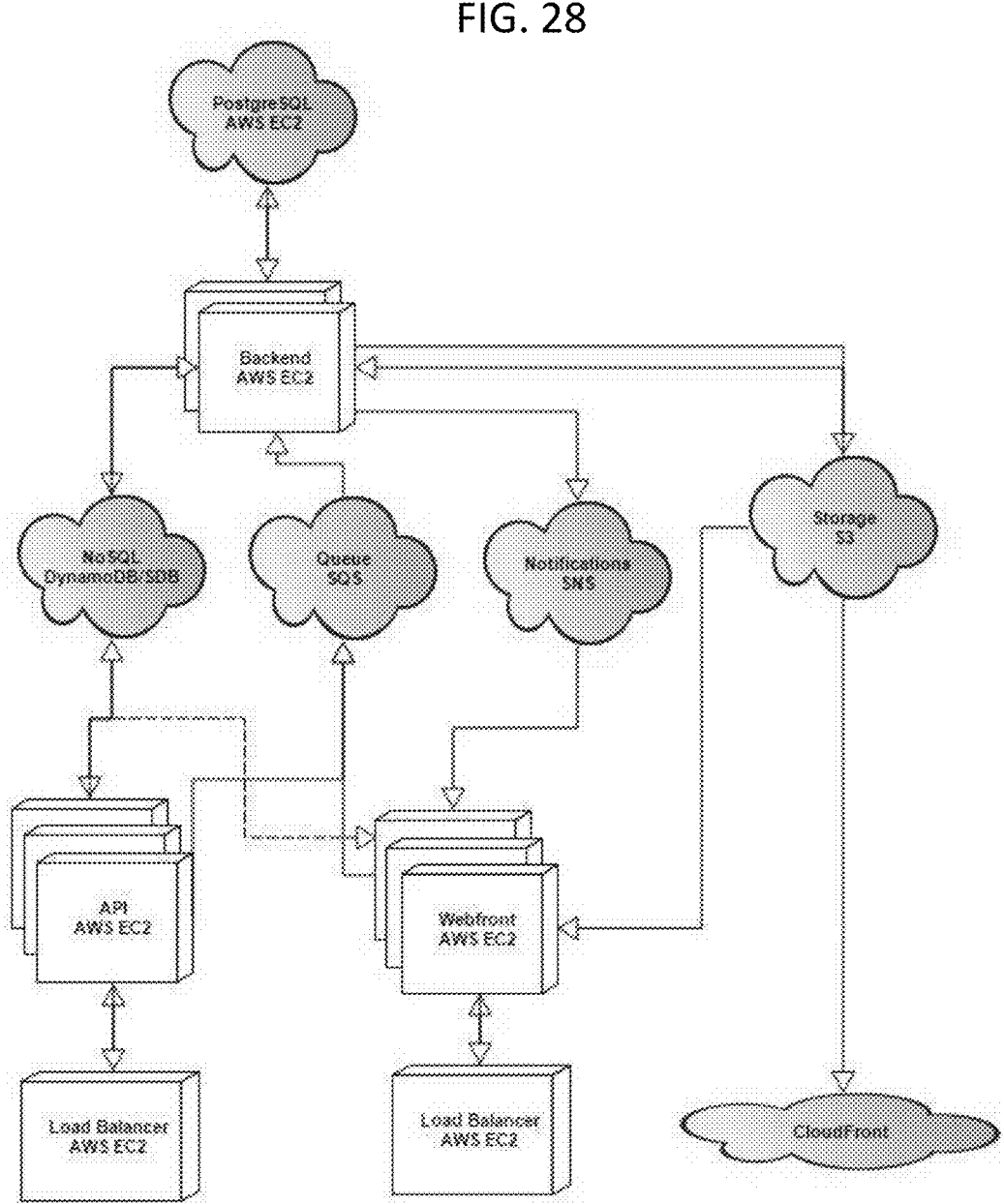
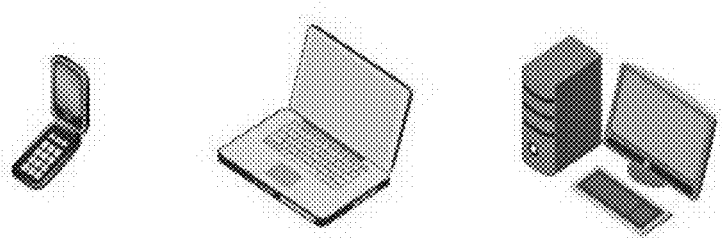

SYSTEM AND METHOD FOR MEASURING BIOLOGICAL FLUID BIOMARKERS

CROSS REFERENCE TO RELATED APPLICATIONS

This application is a continuation-in-part of U.S. application Ser. No. 15/014,526, filed Feb. 3, 2016, which claims priority from U.S. Provisional Patent Application No. 62/130,039, filed Mar. 9, 2015, each of which is incorporated herein by reference in its entirety.

BACKGROUND OF THE INVENTION

1. Field of the Invention

The present invention is generally directed to a system and method including a device for sensing and collecting biological fluid inputs and transmitting inputs to a remote computing device for analyzing the biological fluid inputs.

2. Description of the Prior Art

Generally, biomarkers from biological fluid have significant prognostic and/or diagnostic utility, such as predicting disease, nutritional imbalance, or psychological or physical stress; however, many of the most utilized biomarkers are collected from blood. The ability to predict events through non-invasive means, such as sweat detection, provides great utility to persons under physical stress, particularly individuals in the process of physical activity or exercise. The ability to monitor sweat biomarkers real time and continuously during activity allows an individual to make informed decisions regarding hydration, nutrition, and exertional status, and recovery all variables that moderate physical performance.

For example, hydration status is a predictor of physical performance; dehydration as low as 1% of body mass can impair performance. Prior art detection and treatment, as shown in FIG. 1, is currently at the stages of when symptoms present, performance degrades, and/or injury presents. Determining hydration through sweat biomarkers before dehydration symptoms present has many benefits, such as reducing fatigue, cramps, and headaches. Therefore, developing a device and system for non-invasively obtaining biomarkers, such as through sweat, is needed.

Sweat contains a multitude of biomarkers; any substance aqueously dissolvable in the blood can present in the sweat by way of eccrine glands. The sweat biomarkers can be small molecules, proteins, metabolites, and/or electrolytes. Well-known electrolytes in sweat are sodium and potassium. As shown in FIG. 2, potassium concentration is not dependent upon sweat rate due to the passive diffusive transport of potassium, while sodium and chloride concentrations in sweat are dependent upon sweat rate due to the active transport of sodium. Thus, monitoring sodium or chloride concentrations is an accurate, indirect means of indicating hydration status of an individual. Therefore, developing a sweat biomarker monitoring device that can communicate to an individual real-time biomarker data is needed.

U.S. Pat. No. 6,198,953 for method and system for continuous sweat collection and analysis by Webster, et al. filed Mar. 11, 1999 and issued Mar. 6, 2001 is directed to a method and system of the invention provide especially for continuously obtaining and analyzing, on a real time basis, sweat from a selected area of skin on the body of a person, especially a neonate, being diagnosed for cystic fibrosis, by causing sweating of the selected area of skin, by placing an electrically positive iontophoretic electrode device of a set of said devices over the selected area of skin preferably within a previously placed receiving and holding device which, following the induction of sweat and removal of the electrically positive iontophoretic electrode device, receives a sweat-sensing electrode device that continuously sends electrical signals to sweat analysis circuitry for providing a digital readout of the ionic composition of the sweat.

U.S. Pat. No. 8,388,534 for an apparatus providing skin care information by measuring skin moisture content by Jang, et al. filed Sep. 24, 2007 and issued Mar. 5, 2013 is directed to an apparatus for providing skin care information, the apparatus including: an electrode unit supplying a voltage to a user's skin and detecting a current signal in the user's skin; a measurement control unit measuring the user's skin moisture content and sweat gland activity by using the detected current signal; a data calculation unit deriving skin moisture content information by using the skin moisture content and the sweat gland activity, and generating skin care information corresponding to the skin moisture content information; and an information provider providing the user with the generated skin care information is provided.

U.S. Pat. No. 7,575,549 for an apparatus and method for increasing, monitoring, measuring, and controlling perspiratory water and solid loss at reduced ambient pressure by Miller filed Jul. 30, 2004 and issued Aug. 18, 2009 is directed to a device for increasing, monitoring, and measuring perspiration water and solid loss at reduced ambient pressure, comprising a sealed chamber capable of maintaining less than atmospheric pressure for an extended period of time and a gasket-sealed door accessing the chamber. An algorithm allowing for continuous calculations of sweat loss and fluid replacement requirements of the occupant of the chamber is disclosed.

US patent application 2014/330,096 for performing a physiological analysis with increased reliability by Brunswick filed Nov. 12, 2012 and issued Nov. 6, 2014 is directed to a method for performing an electrophysiological analysis implemented in a system includes: a series of electrodes to be placed on different regions of the human body; a DC voltage source controlled so as to produce DC voltage pulses; a switching circuit for selectively connecting the active electrodes to the voltage source, the active electrodes forming an anode and a cathode, and for connecting at least one other high-impedance passive electrode used to measure the potential reached by the body; and a measuring circuit for reading data representative of the current in the active electrodes, and data representative of the potentials generated on at least certain high-impedance electrodes in response to the application of the pulses, the data allowing a value to be determined for the electrochemical conductance of the skin.

US patent application 2014/350,432 for assessment of relative proportions of adrenergic and cholinergic nervous receptors with non-invasive tests by Khalfallah and Brunswick filed Aug. 8, 2014 and issued Nov. 27, 2014 is directed to a system and method for assessing relative proportions of cholinergic and adrenergic nervous receptors in a patient is disclosed. The system includes: an anode, a cathode, and passive electrode for placement on different regions of the patient body. The method generally includes: applying DC voltage pulses of varying voltage values to stress sweat glands of the patient, collecting data representing the current between the anode and the cathode and the potential of the anode, the cathode, and the passive electrode for each of the different DC voltage, and computing data representing the electrochemical skin conductance of the patient. The computed data representing the electromechanical skin conductance of the patient is reconciled with reference data from control patients having known relative proportions of cholinergic and adrenergic nervous receptors. Thus, the relative proportions of cholinergic and adrenergic nervous receptors in the patient can be determined.

US patent application 2015/019,135 for motion sensor and analysis by Kacyvensky, et al. filed Jun. 3, 2014 and issued Jan. 15, 2015 is directed to the performance of an individual being monitored based on measurements of a conformal sensor device. An example system includes a communication module to receive data indicative of a measurement of at least one sensor component of the conformal sensor device. The sensor component obtains measurement of acceleration data representative of an acceleration proximate to the portion of the individual. A comparison of a parameter computed based on the sensor component measurement to a preset performance threshold value provides an indication of the performance of the individual.

Published article by Liu, et al. in Conf Proc IEEE Eng Med Biol Soc, 2014:1678-81, discusses the implementation of a microfluidic conductivity sensor—a potential sweat electrolyte sensing system for dehydration detection.

Although biomarkers in sweat are appreciated, specifically electrolytes and glucose, a system and method is still lacking that continuously analyzes sweat biomarkers in real time and transmits data to a user, which informs the user of his or her health status.

SUMMARY OF THE INVENTION

The present invention presents a system and method including a device for sensing and collecting biological fluid inputs and transmitting inputs via a wireless network to a remote computing device for analyzing the biological fluid inputs and fluid biomarkers, calculating biomarker data, and storing the data in a database and/or on the computing device and/or on a remote computer server.

The system includes an apparatus or device including at least one electrochemical sensor, a microcontroller, and a transceiver antenna coil; at least one remote transceiver device; and at least one remote computer server. The apparatus analyzes at least one biological fluid biomarker, calculates at least one output datum of the at least one biological fluid biomarker, and transmits the at least one output datum to the at least one remote transceiver device. The at least one remote transceiver device transmits the at least one datum with the at least one remote computer server or at least one remote computing device for database or storage. The apparatus and the at least one remote transceiver device have real-time or near-real-time two-way communication.

The method includes the steps of providing an apparatus including at least one electrochemical sensor, a microcontroller, and a transceiver antenna coil; at least one remote transceiver device; and at least one remote computer server. The at least one remote transceiver device and the apparatus being operable for two-way cross-communication in real-time or near-real-time. The electrochemical sensor sensing at least one biomarker, which creates a voltage. The microcontroller converting the at least one biomarker into at least one output datum using at least one algorithm. The at least one remote transceiver device inputting modifying variables into the at least one algorithm via the two-way communication with the apparatus. The transceiver antenna coil transmitting the at least one output datum to the at least one remote transceiver device via the two-way communication with the apparatus. The at least one remote transceiver device sharing or transmitting the at least one datum with the at least one remote computer server or device or database for storage.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 1 shows a chart demonstrating biomarker types, changes in biomarker levels during progressive stages of injury, and physiological presentations associated with each stage of injury.

FIG. 2 shows a chart relating sweat rate to concentration of electrolytes.

FIG. 3 shows the multiple layers and associated parts of the sensor apparatus and a top perspective view of the complete sensor apparatus.

FIG. 11A shows a table of various sweat characteristics including basic ratio for sweat flow rate, body surface area calcs, and sweat loss & body mass loss calcs.

FIG. 11C shows tables including work level, zone, SFR, mV ratio, Na Loss, K Loss, Typ Wt, sweating rate and sweat sodium concentration and a chart of frequency vs. Na loss.

FIG. 11D shows a table of sweat stds for a typical user.

FIG. 12A shows a table of basic electrolyte concentration conversions.

FIG. 12C shows a table of basic mV ratios.

FIG. 13A shows thresholds for electrolyte concentrations.

FIG. 13B shows a table of user input at session start, input from phone, and input from sensor.

Figure 27:
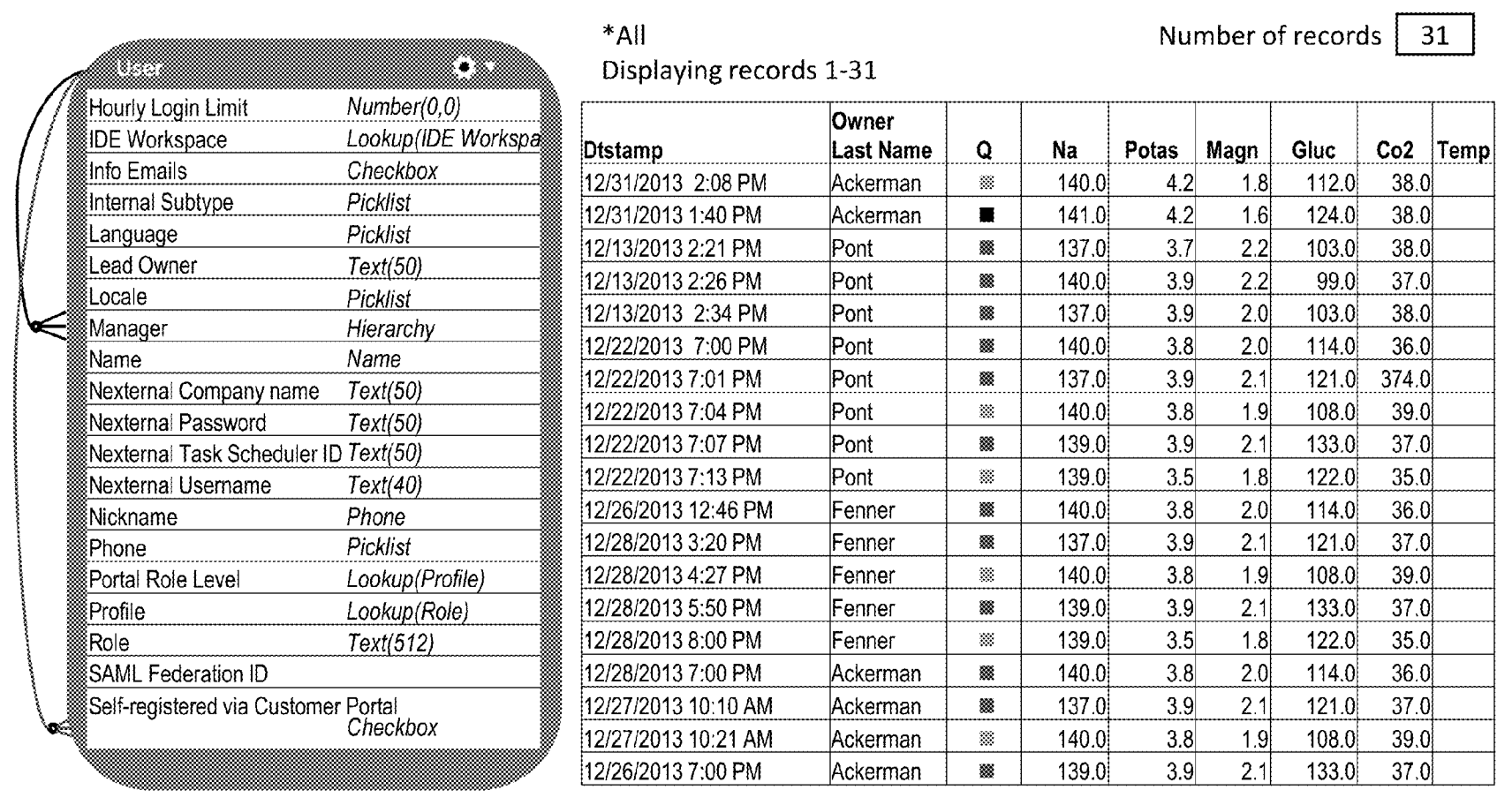

FIG. 27 shows an image of a user data base on the remote computer server.

FIG. 28 shows a diagram of the generic cloud architecture.

FIG. 37 C shows another side perspective view of a sensor with a liquid ionophore coating.

DETAILED DESCRIPTION

The present invention provides systems and methods including a device for sensing and collecting biological fluid inputs and transmitting inputs to a remote computing device for analyzing the biological fluid inputs or analyzing biological fluid biomarkers, calculating biomarker data, and storing the data in a database and/or on the computing device and/or on a remote computer server.

Figure 4:
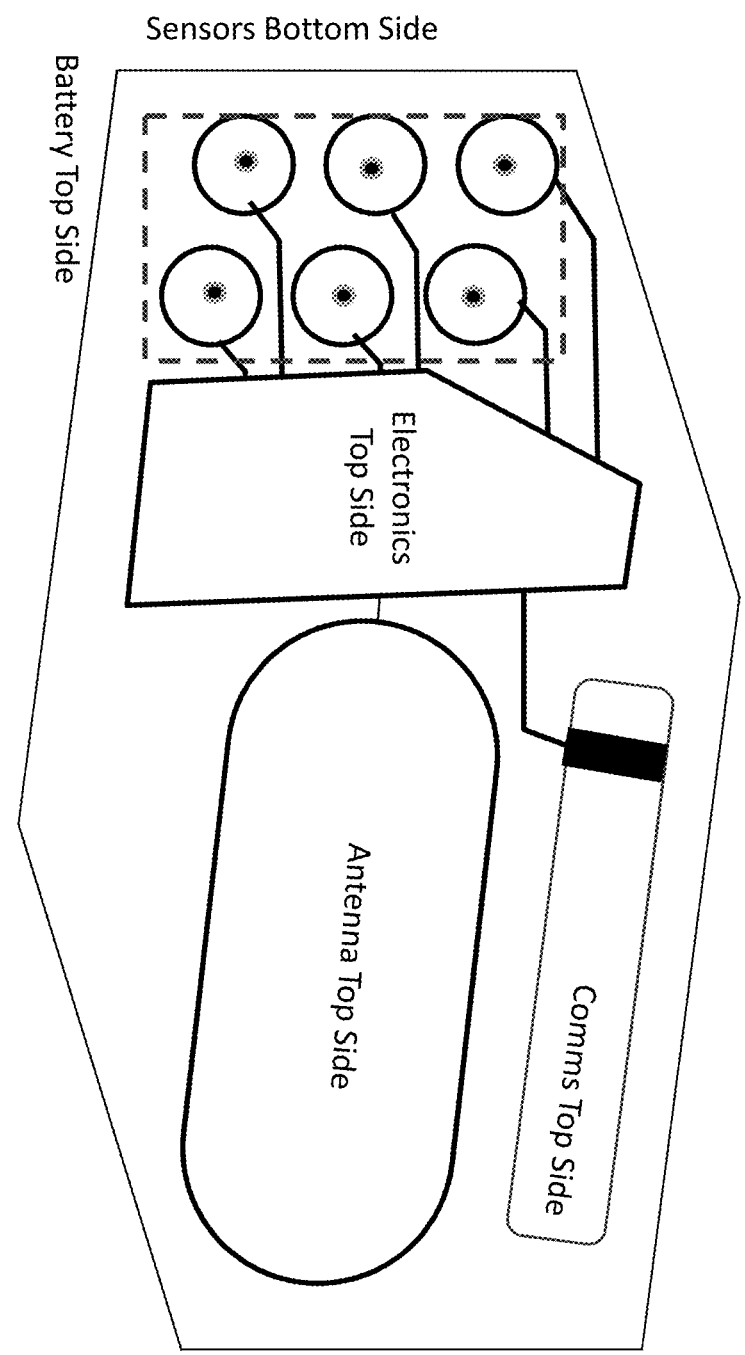
FIG. 4 shows a perspective top view of a flexible electronic layer on the bottom adhesive layer.
Figure 5:
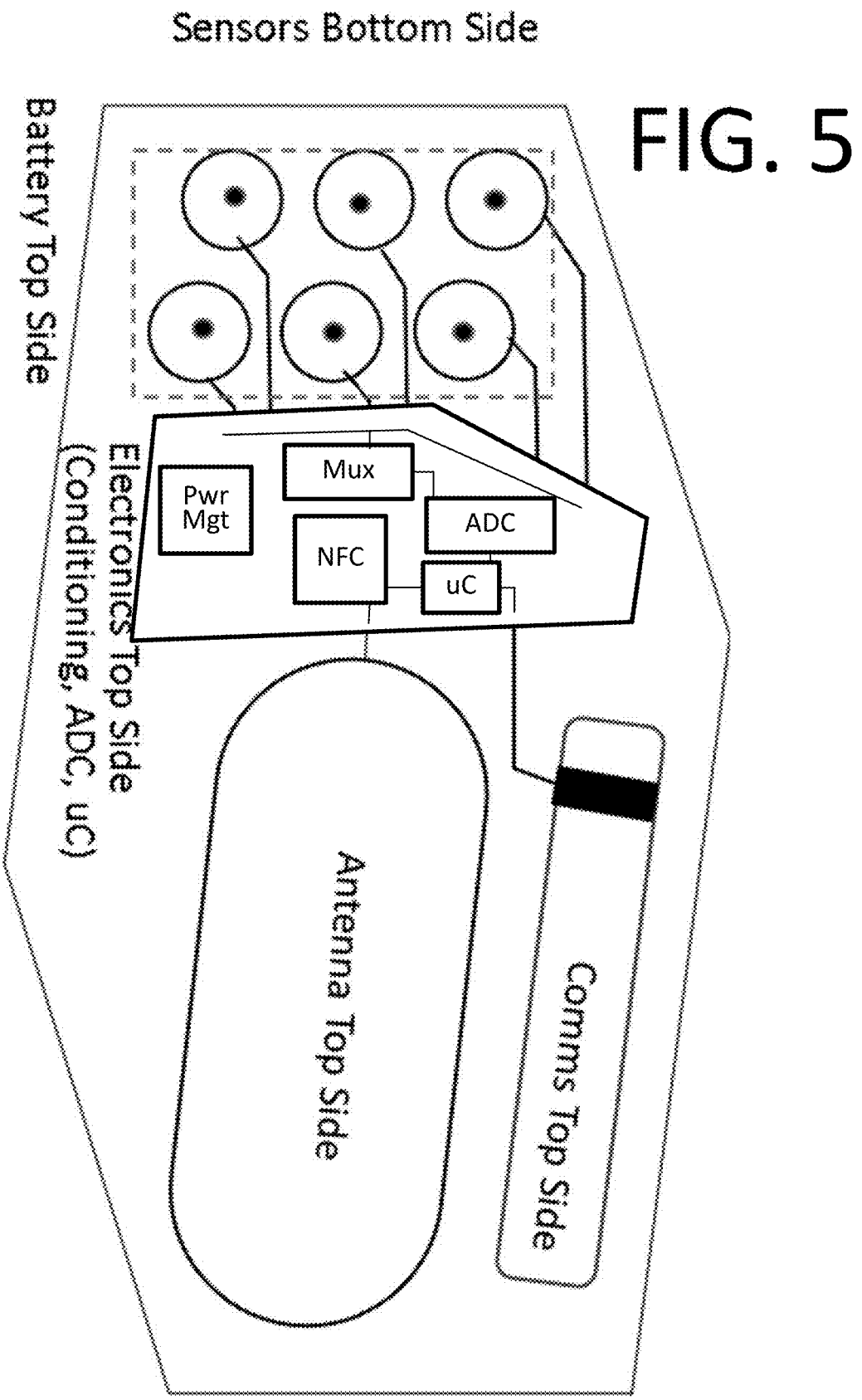
FIG. 5 shows a complete flexible electronic layer.
Figure 6:
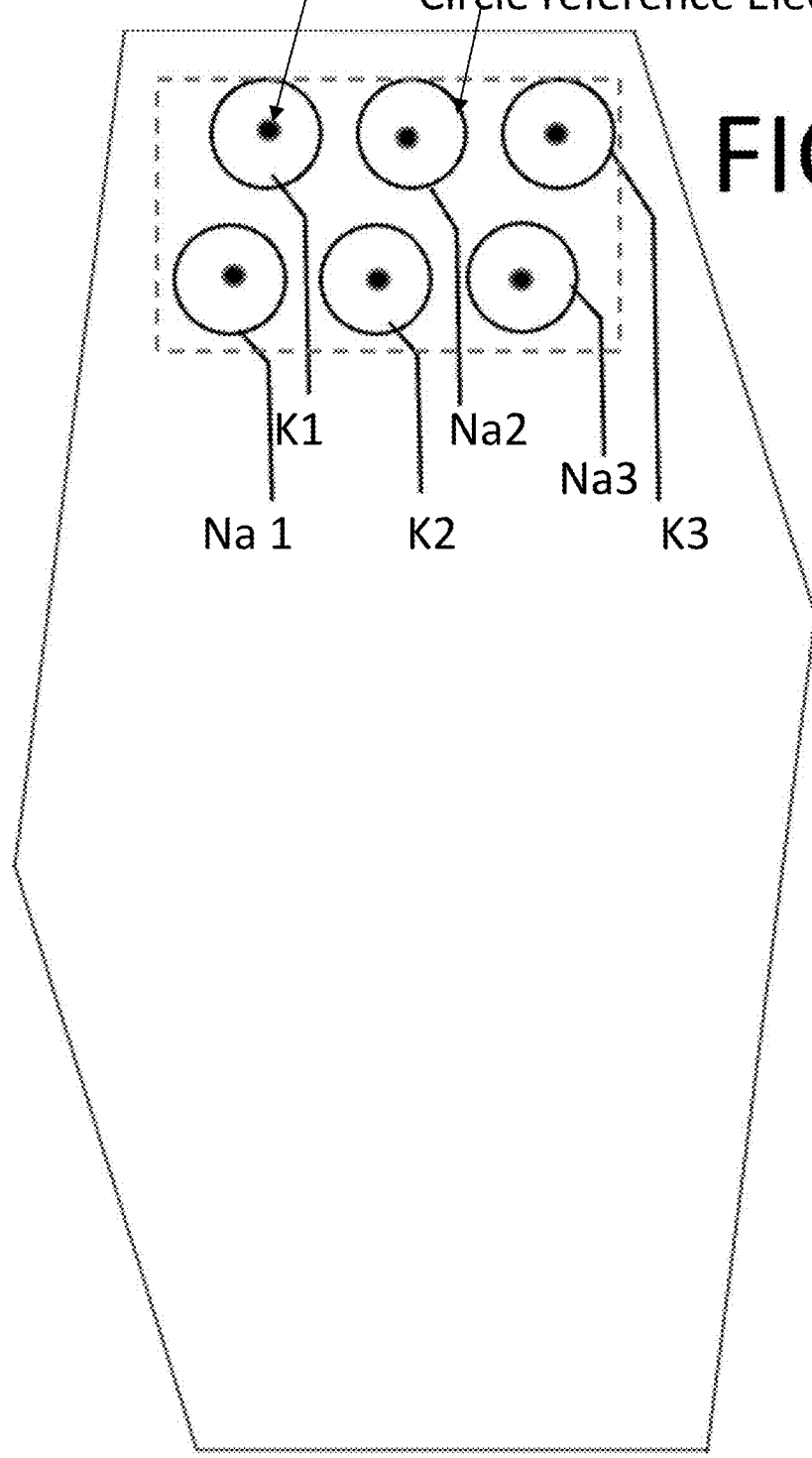
FIG. 6 shows a separated layer of electrochemical sensors.
Figure 8:
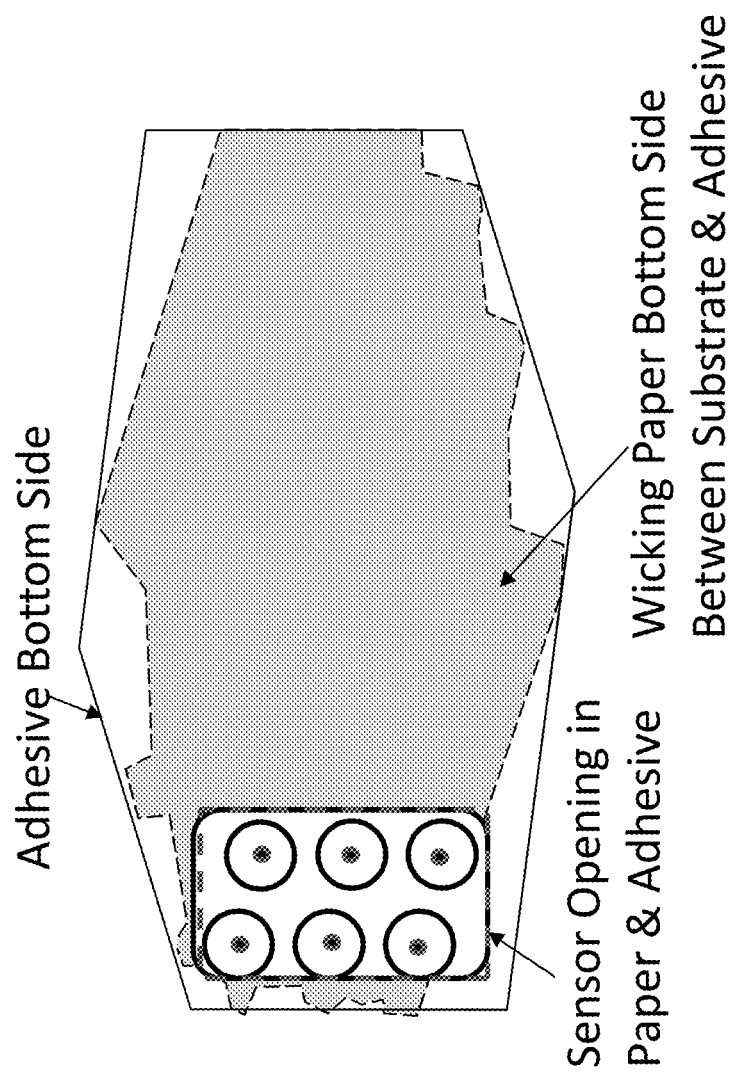
FIG. 8 shows a top perspective view (top) and bottom perspective (bottom) view of a complete sensor apparatus.

One component of the system is a sensor apparatus or device for sensing sweat biomarkers. FIG. 3 illustrates a multi-layered apparatus or device that includes a double-sided adhesive layer, a filter paper, an electronic layer, and a woven top adhesive. More specifically, the device is flexible and multi-layered, wherein the layers comprise the following: a macrofluidic, double-sided adhesive layer; an electronic layer comprising at least one electrochemical sensor, a microcontroller, and a transceiver antenna coil; a microfluidic management layer; and a vapor porous, top protective layer. The macrofluidic, double-sided adhesive layer is intimately adhered to the skin. The electronic layer is intimately adhered to the macrofluidic, double-sided adhesive layer, as shown in FIG. 4. The microfluidic management layer circumferentially surrounds the at least one electrochemical sensor of the electronic layer. The vapor porous, top protective layer is placed on and completely covers the microfluidic management layer and electronic layer. The vapor porous, top protective layer is intimately adhered to the macrofluidic, double-sided adhesive layer. The fully fabricated sensor apparatus is shown in FIG. 8. Preferably, the length of the apparatus is approximately 76.1 mm. In one embodiment, the adhesive of the apparatus is Double Coated Polyester Nonwoven Tape (commercially available as 3M 9917 as of this writing). In another embodiment, the adhesive of the apparatus is Tan Tricot Knit Tape (commercially available as 3M 9926T as of this writing). The design of the microfluidic layer improves flow control and decreases patch layer delamination during high sweat volume use cases.

Figure 34:
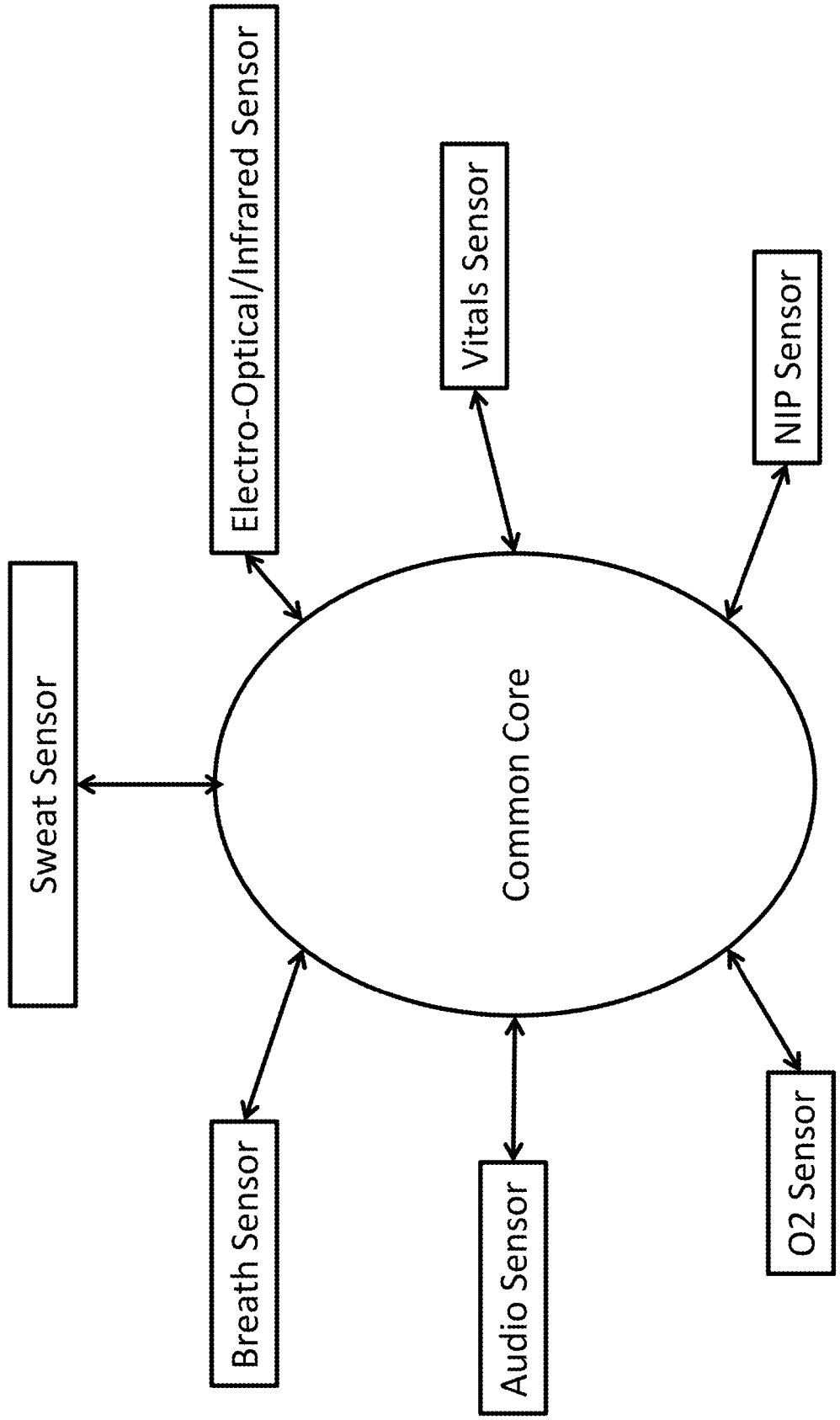
FIG. 34 shows a diagram of a suite of sensors in addition to a sweat sensor.

FIG. 34 shows a diagram illustrating a suite of sensors in addition to a sweat sensor, including a non-invasive penetration (NIP) sensor, an audio sensor, a vitals sensor, an electro-optical/infrared sensor, an oxygen sensor, a breath sensor, and a sweat sensor. In one embodiment the sensor includes at least two of the sensors in FIG. 34. In another embodiment, one of the suite of sensors is the only sensor utilized. One or more of the sensors is embedded in the skin in one embodiment of the present invention. An embedded sensor preferably mimics the composition and behavior of cells. The electro-optical/infrared sensor may include a fluorescent signal sensor. In one embodiment, a reader sends an excitation light through the skin to the biosensor, which then emits a fluorescent light proportional to the amount of biochemical measured.

Figure 35:
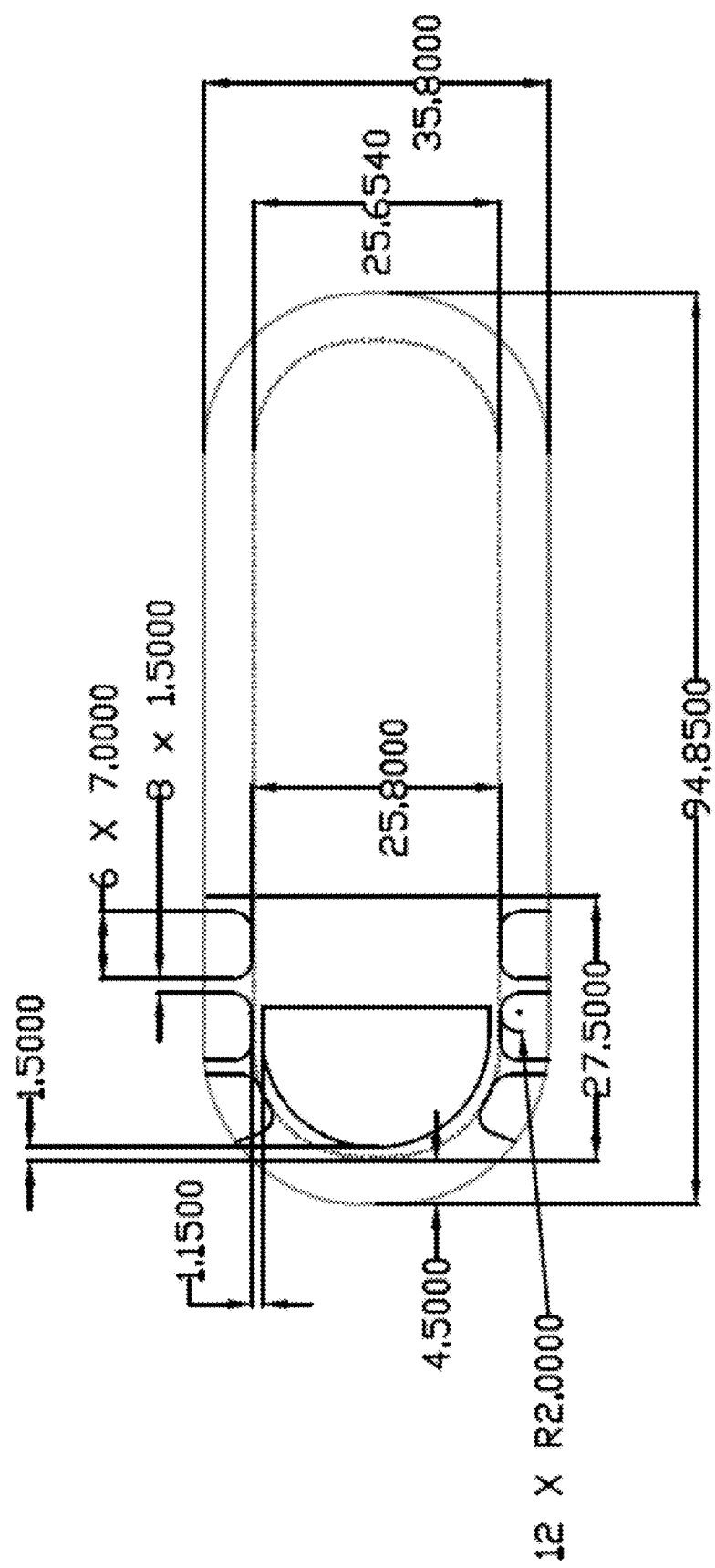
FIG. 35 shows a top perspective view of one embodiment of the sensor apparatus.

FIG. 35 shows a top perspective view of one embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 35 are in MM or VOS, as appropriate.

Figure 36:
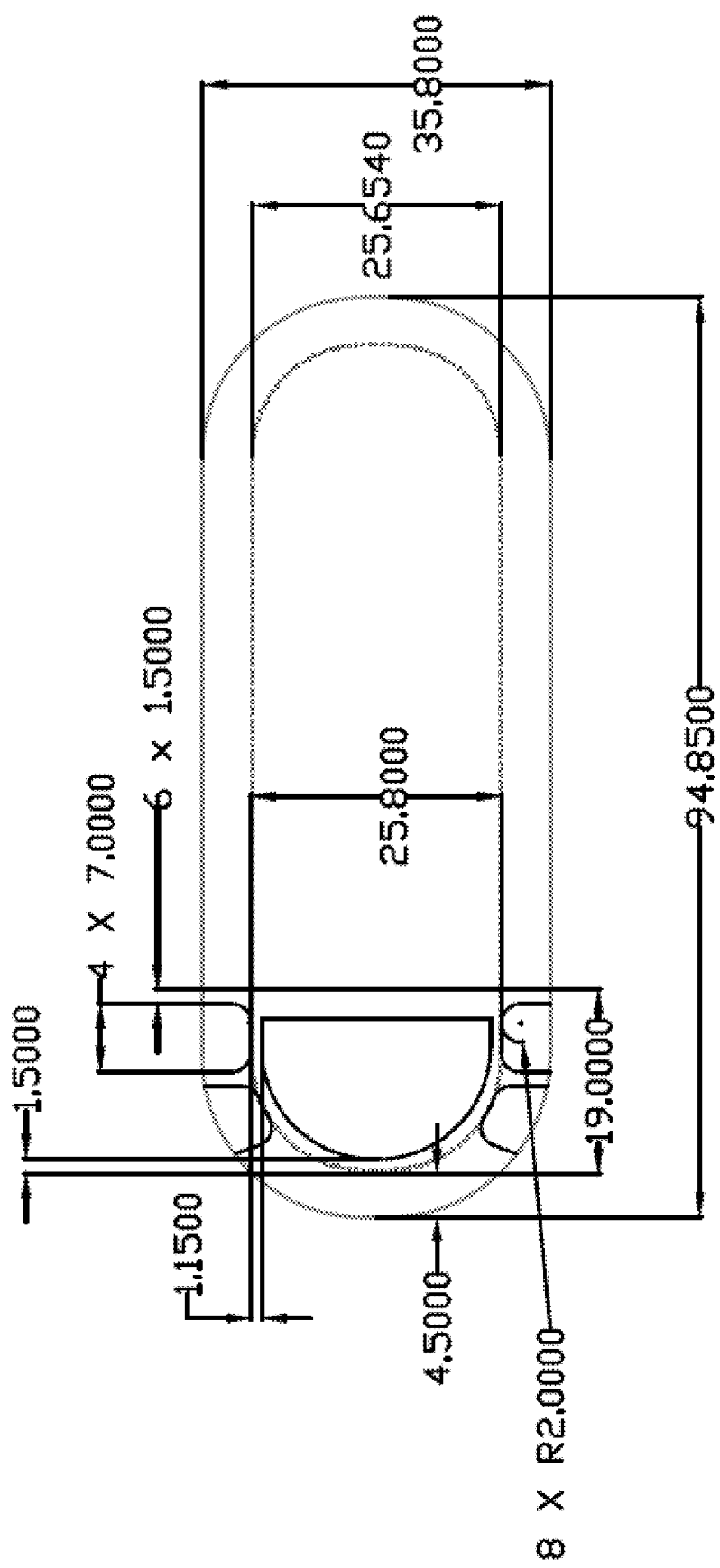
FIG. 36 shows a top perspective view of another embodiment of the sensor apparatus.

FIG. 36 shows a top perspective view of another embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 36 are in MM or VOS, as appropriate.

Figure 9:
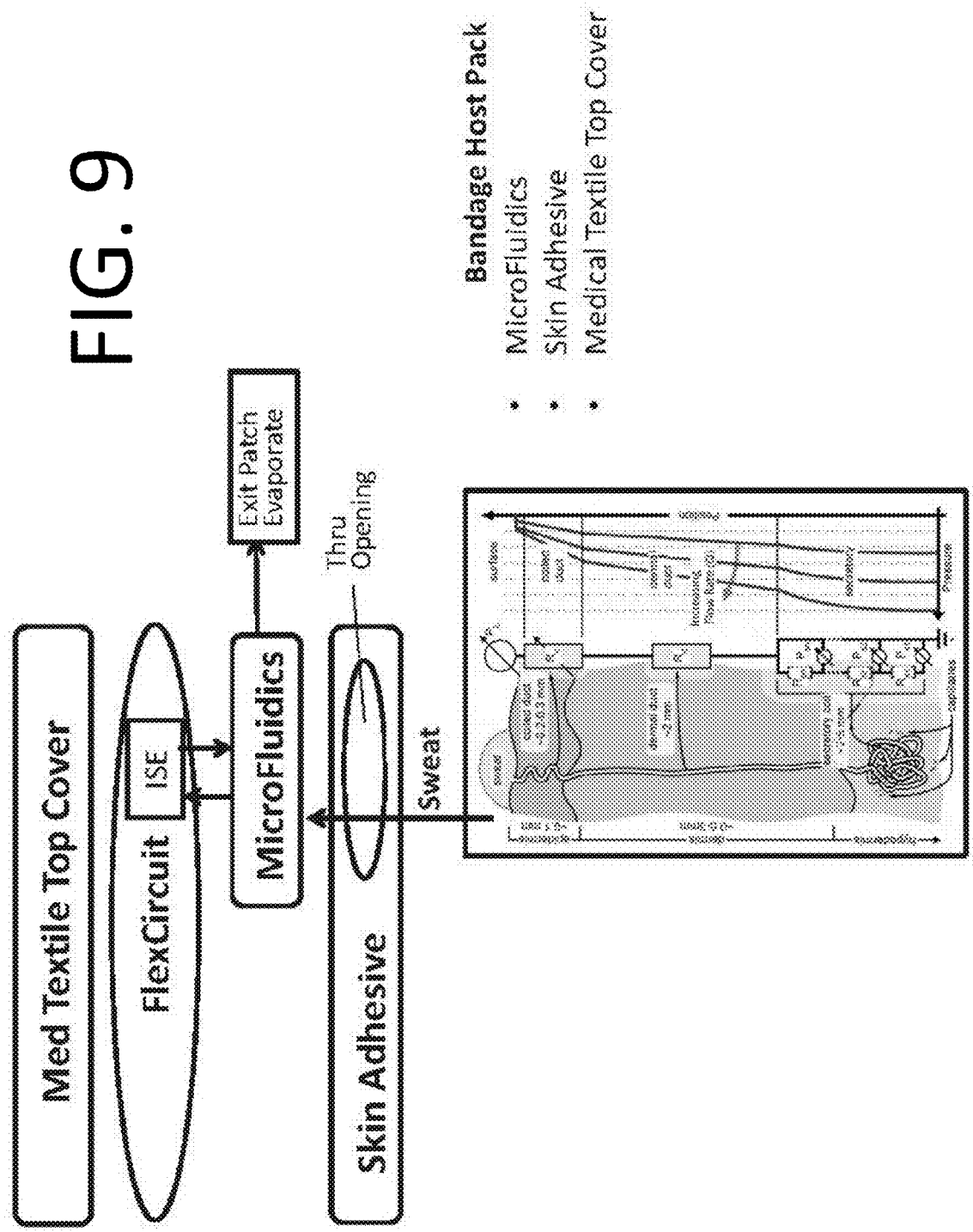
FIG. 9 shows a diagram of the sweat path through the sensor apparatus.

The sensor apparatus is designed to allow sweat to flow through laser cut, macrofluidic pores in the skin adhesive layer, as shown in FIG. 9. Sweat then flows through a filter to the electronics layer, specifically the electrochemical sensor unit, where biomarkers may contact the electrodes of the electrochemical sensor unit. The sweat evaporates through the woven textile protective top layer. The evaporation affords improved and continuous sweat flow into the sensor apparatus. This wicking ensures sweat sensing measures are consistently using new sweat samples rather than static or diluted samples. In one embodiment, the wicking and sweat flow rates range from 0% to 5% Total Body Loss/hr (instant equivalent sweat loss rate) or equivalent to 11.5 L/hr total loss.

The present invention further includes a device with a small amount of ionophore polymer on the active electrodes to filter/prevent untargeted ions to reach the electrode. Sensor functionality and accuracy require precision placement with proper thickness of a small amount of ionophore polymer in one embodiment. The amount is approximately 2 microliters with a designated viscosity placed in a clean assembly environment to completely cover the exposed active electrode on the skin-facing side of the flexcircuit. The coating shall preferably not exceed more than 0.5 mm from the edge of the electrode. In one embodiment, the ionophore polymer is cured. In another embodiment, the curing takes place using heat and/or light to accelerate drying without changing the ionophore selectivity characteristics.

In one embodiment, the sensor is calibrated. Preferably, a human user calibrates the sensor using actual test results and feedback from the sensor. Advantageously, human user calibration or human use self-calibration (H-SCAL) provides for more accurate data when compared with calibration of sensors solely in the laboratory. Actual human test data is compared to external sweat loss ground truth obtained from highly accurate scales. The external data is utilized to adjust several factors for a human user. Specifically, the adjustments provide for correction of a collection of diminutive and/or major error sources to improve the overall accuracy of the system.

Figure 7:
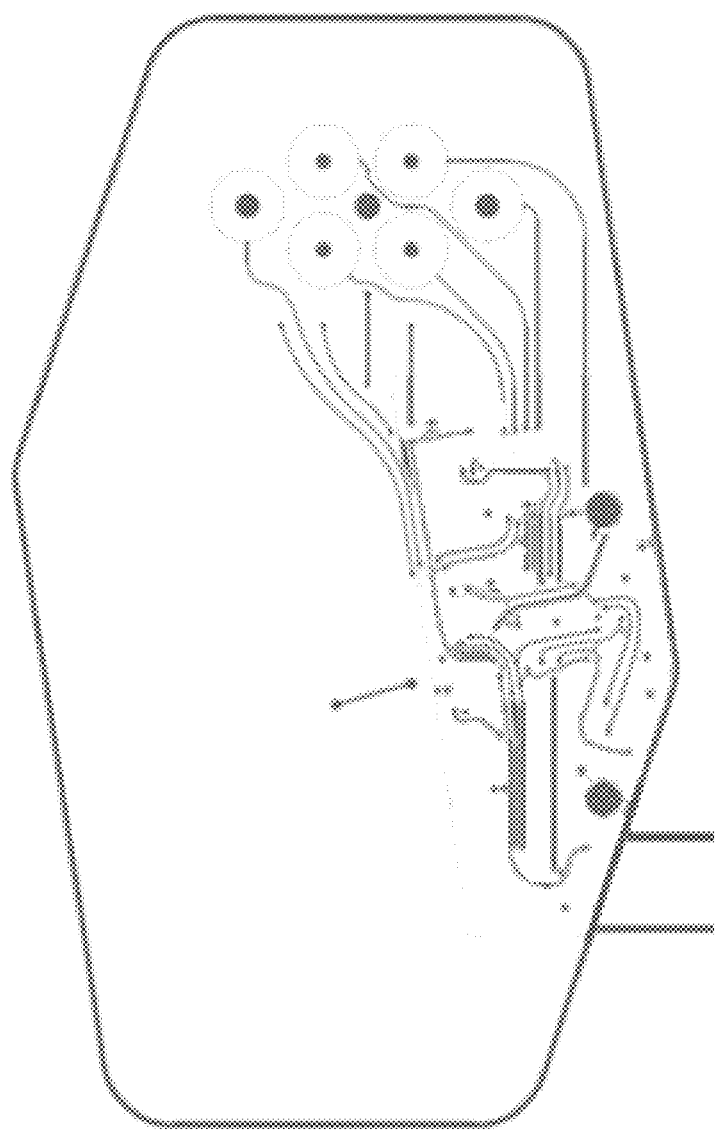
FIG. 7 shows the electrochemical sensors.
Figure 15:
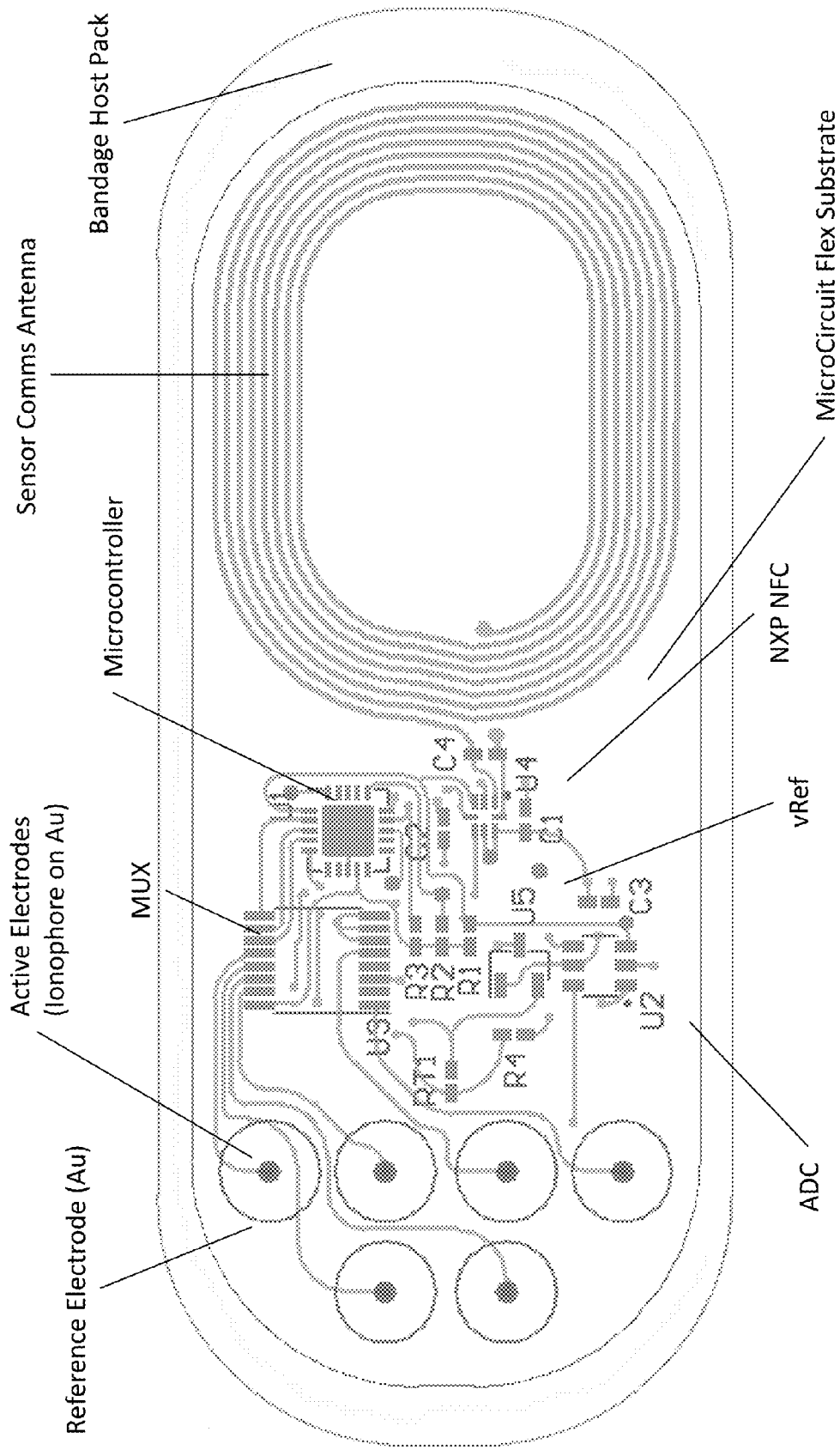
FIG. 15 shows a diagram of components within the sweat sensor subsystem.

The sensor apparatus includes sweat sensor subsystem, as shown in FIG. 15, which includes a microcontroller that receives multiple input data, which are input from multiple sources. A first source is biological fluid, preferably sweat, although alternative fluids may be used. The sweat contains a variety of analytes, such as, by way of example and not limitation, electrolytes, small molecules, proteins, and metabolites. Exemplary analytes include substances including sodium or potassium. In one embodiment, the sensor apparatus is operable to sense sodium in a dynamic range from about 0 mM to about 120 mM, with normal ranges in humans being about 20 mM to about 100 mM. In another embodiment, the sensor apparatus is operable to sense potassium in a dynamic range from about 0 mM to about 40 mM, with normal ranges in humans being about 5 mM to about 20 mM. In one embodiment, the sensor has a response time of about 60 seconds with about a 90% response. Other analytes include oxygen, glucose, ammonium, and interleukins. In one embodiment, the sensor is operable to analyze the analytes at a pM level, preferably in the 1-10 pM range or even below 1 pM (the sub-pM level). These analytes are collected at the electrochemical sensor, as shown in FIG. 7, which houses reference (preferably standard) and active electrodes, wherein, by example and not limitation, the electrodes are silver, zinc, copper, gold, platinum, rhodium, carbon or a combination thereof. In one embodiment, the apparatus has an embedded dot-circle configuration for a reference electrode to improve stability through less interference. Additionally, gold probes or electrodes are used in one embodiment to improve stability and reduce production costs. The apparatus also includes a microprocessor, multiplexer (mux), ADC, and optimized on board processing for real time, pre-transmission sensor signal conditioning in another embodiment.

Figure 40:
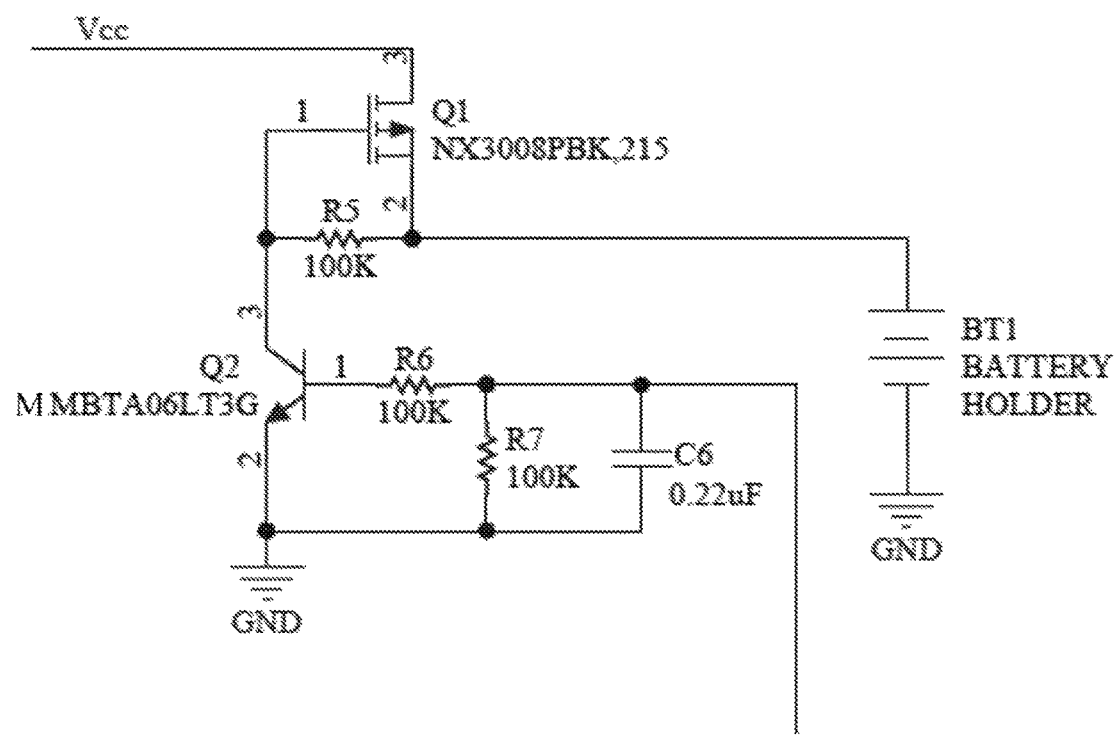
FIG. 40 shows a battery latch mitigation capacitor placement.

Unique human induced electromagnetic interference (H-EMI) sometimes cause interference and produce inaccurate measurements from the sensor apparatus. Specifically, human induced anomalies affect flex circuit functionality, performance, and reliability. Variations in the location of the sensor on the human body as well as human skin variations between people can cause unpredictable flex circuit behavior that is not readily apparent in lab settings. Through testing on humans, various embodiments and solutions to H-EMI have been developed. In one embodiment, hardware components are placed to mitigate the human use electromagnetic interference effects on flex circuits. Specifically, the placement of capacitors compensates for intermittent power variations. Additionally, strategically placed Kapton reinforcements (or other polyimide components) further mitigate EMI disturbances resulting from human use electromagnetic interference. Specifically, capacitors are utilized on power/battery latching circuits to mitigate human motion artifacts impacting measurement cycles. FIG. 40 shows a battery latch mitigation capacitor placement. The values included in FIG. 40 are for purposes of illustration by example and in no way limit the values which are utilized in the present invention.

Figure 41:
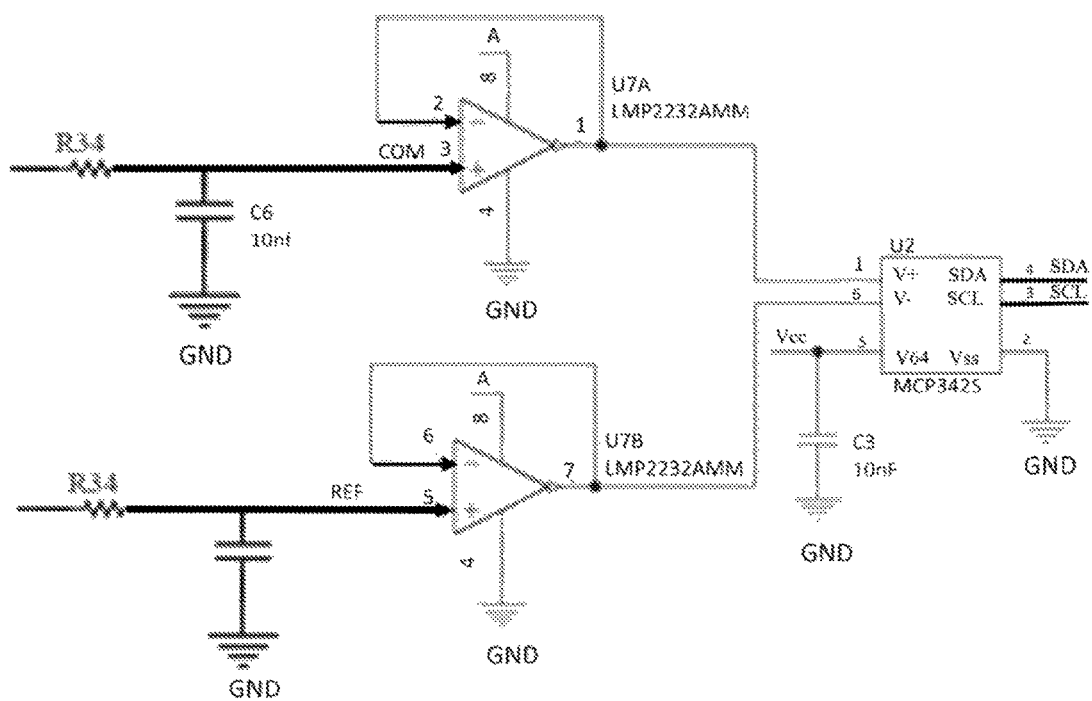
FIG. 41 shows an RC configuration with ground reference.
Figure 42:
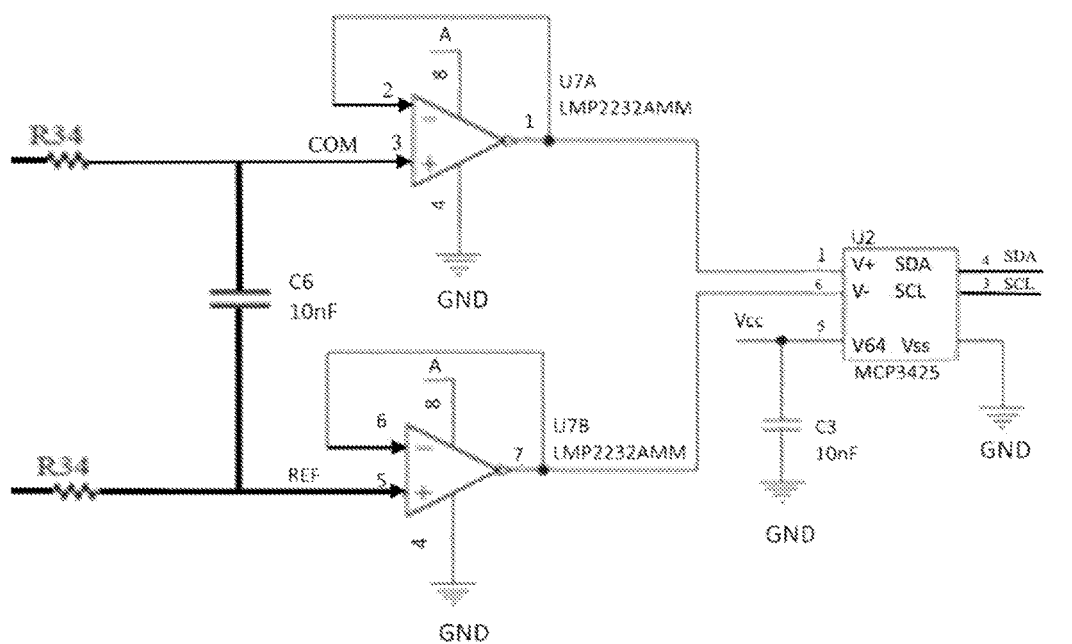
FIG. 42 shows an RC configuration with differential measurement.
Figure 43:
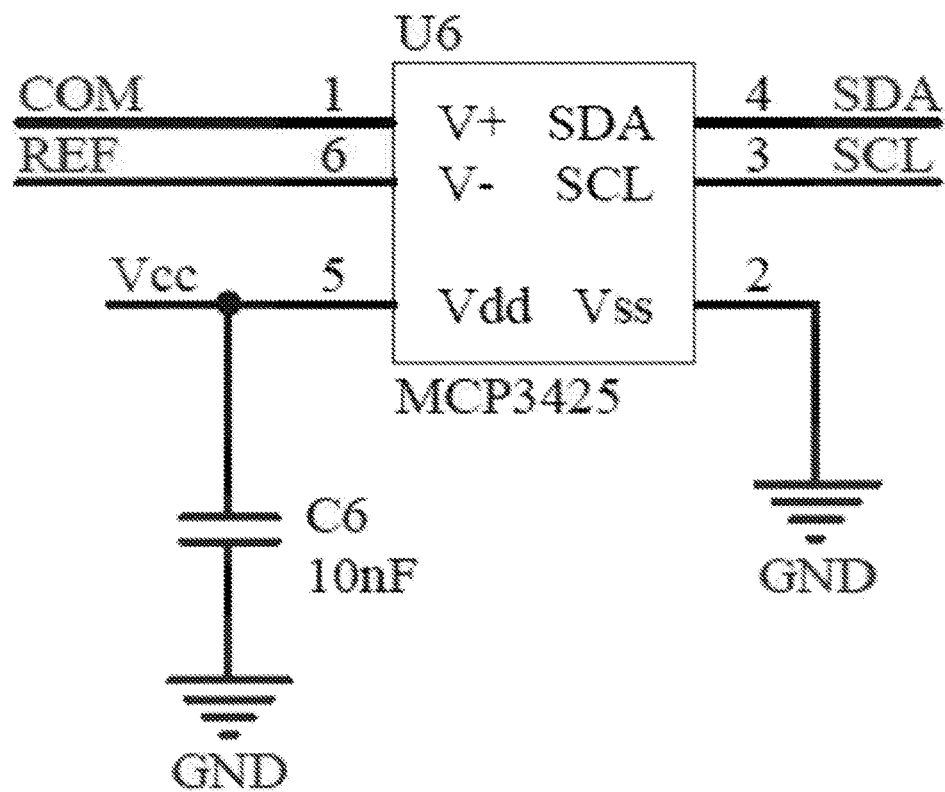
FIG. 43 shows an example of cap placement Vcc to Ground for supply voltage stability and/or noise immunity.

Adjustments in firmware running on a microcontroller also offset EMI in some embodiments. In another embodiment, adjustments to filtering (preferably by adding specific RLC components) and noise suppression offset EMI. Improved measurement electronics input design and sampling methods also mitigate H-EMI. In one embodiment, input design involves complex impedance related to the RLC (mostly R and C) components to condition sensor inputs to overcome motion artifacts manifest from the human sensor interface and input buffering methods to reduce measurement electronics impact on sensor measurements (Heisenberg Uncertainty). FIG. 41 shows an RC configuration with ground reference. FIG. 42 shows an RC configuration with differential measurement. FIG. 43 shows an example of cap placement Vcc to Ground for supply voltage stability and/or noise immunity. Firmware branching logic preferably differentiates between power on cycle and motion induced power variations.

The present invention also includes sensor embodiments which are operable under the most demanding physical environments, and in particular, athletic use cases. Specifically, a durable sensor is needed for these cases because of exposure to violent impact shock, speed changes, motion intensity, exposure to water, etc. Strengthening the flex circuit and electronic layouts minimize use case impacts on the sensor. Additionally, advanced flex circuit protection minimizes impacts upon the sensor. Advanced flex circuit protection includes strategic flex circuit mix with rigid boards and/or application-specific integrated circuit (ASIC) miniaturization. Advanced rubberized casings and microfluidics based on crystal fiber technology are also utilized in one embodiment. Specifically, the present invention includes the aforementioned adjustments to the sensor head of the sensor apparatus. Sensor heads accommodate a variety of motion factors, including flex, stretch, sliding, and shock loading. In one embodiment, the present invention utilizes multiple sensor configurations to accommodate individual sensor disruption and/or failure.

In one embodiment, the sensor head is detachable and reattachable. The sensor head is attached via z-axis tape or hot bar soldering in one embodiment. In another embodiment, there is a standardized interconnection. In yet another embodiment, the sensor head pinout is selectable from the multiplexer side. In one embodiment, uC and a RF antenna are integrated with fabric. In yet another embodiment, two part encryption is utilized. RFI and shielding as well as adding layers to the board to provide additional ground planes and/or metallized fabric in dressing are also utilized.

Additionally, flexibility in most components of the sensor apparatus is not desired. FR4 is utilized in a preferred embodiment. The sensor head is the only flexible portion of the sensor in one embodiment, as the sensor head requires flex and adhesion to the human. However, for embodiments in which flexibility is desired, a variety of flexible substrates are utilized.

Another embodiment of the present invention includes adding a layer or row of 0 ohm resistors on either side of the multiplexer. Additionally, buffer amps are utilized either before or after the multiplexer. In an alternative embodiment, higher impedance ADC is utilized. Fault detection and isolation is also used in the systems and methods of the present invention.

Figure 37A:
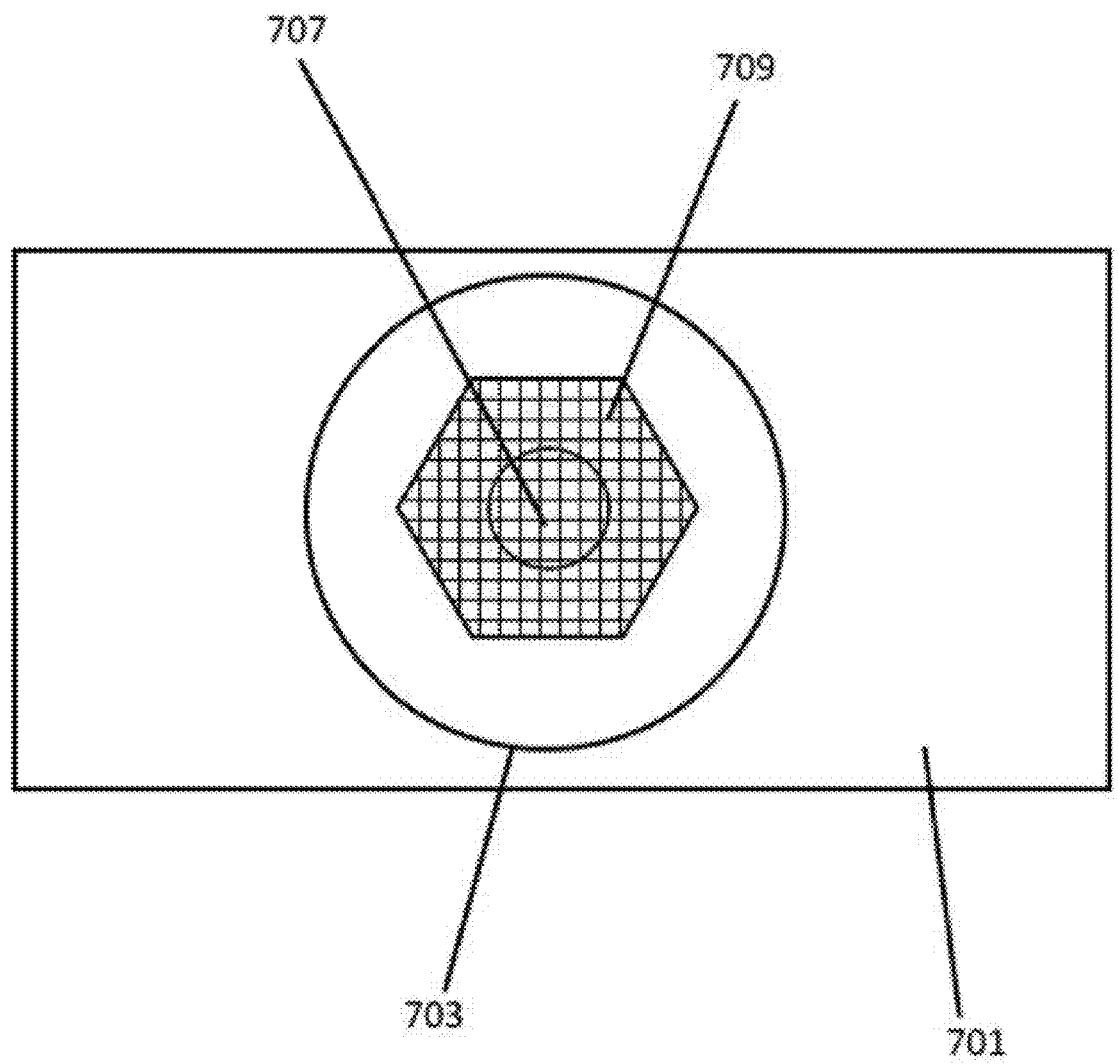
FIG. 37A shows a top perspective view of a sensor with a liquid ionophore coating.

FIG. 37A shows a top perspective view of a sensor with a liquid ionophore coating. A circuit board or other substrate 701 includes a copper trace or other conductive material/circuit element 703, an ionophore or any material applied using a liquid deposition method 705, and copper or other conductive material 707. The ionophore 705 preferably covers the copper or other conductive material 707.

Figure 37B:
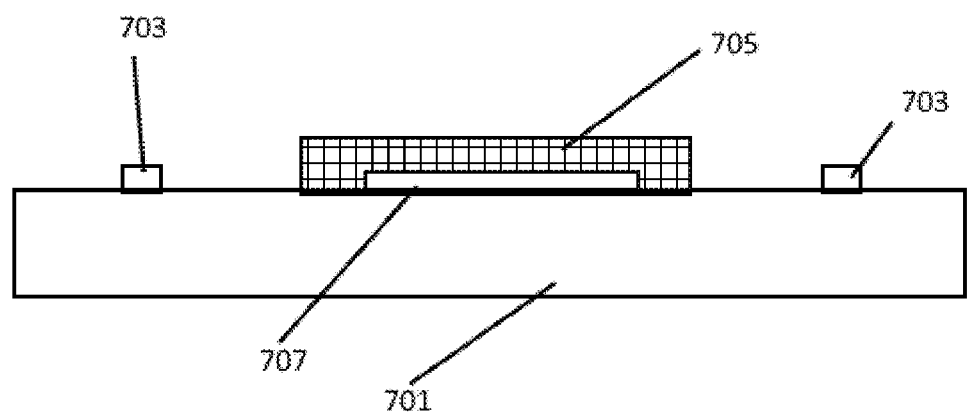
FIG. 37 B shows a side perspective view of a sensor with a liquid ionophore coating.
Figure 37C:
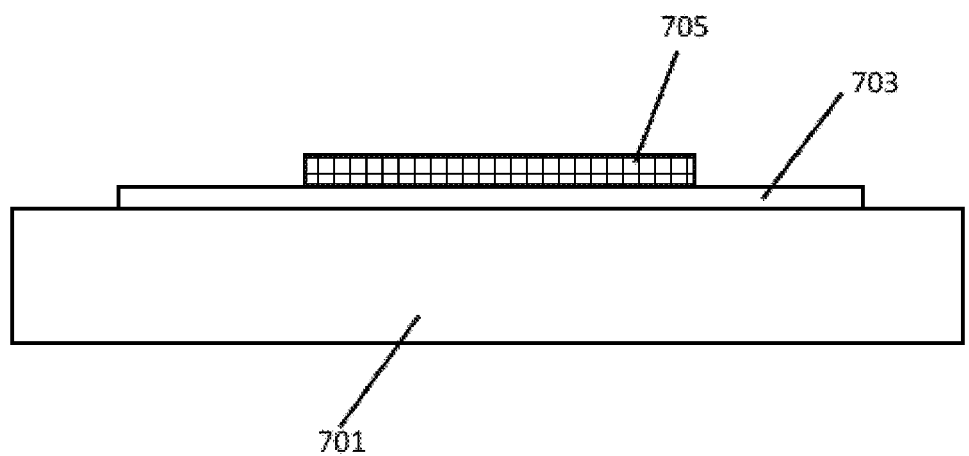

FIG. 37 B shows a side perspective view of a sensor with a liquid ionophore coating.

FIG. 37 C shows another side perspective view of a sensor with a liquid ionophore coating.

One sensor head embodiment of the present invention includes a Ring-Reference design. This design preferably solves issues with surface tension management.

Figure 39A:
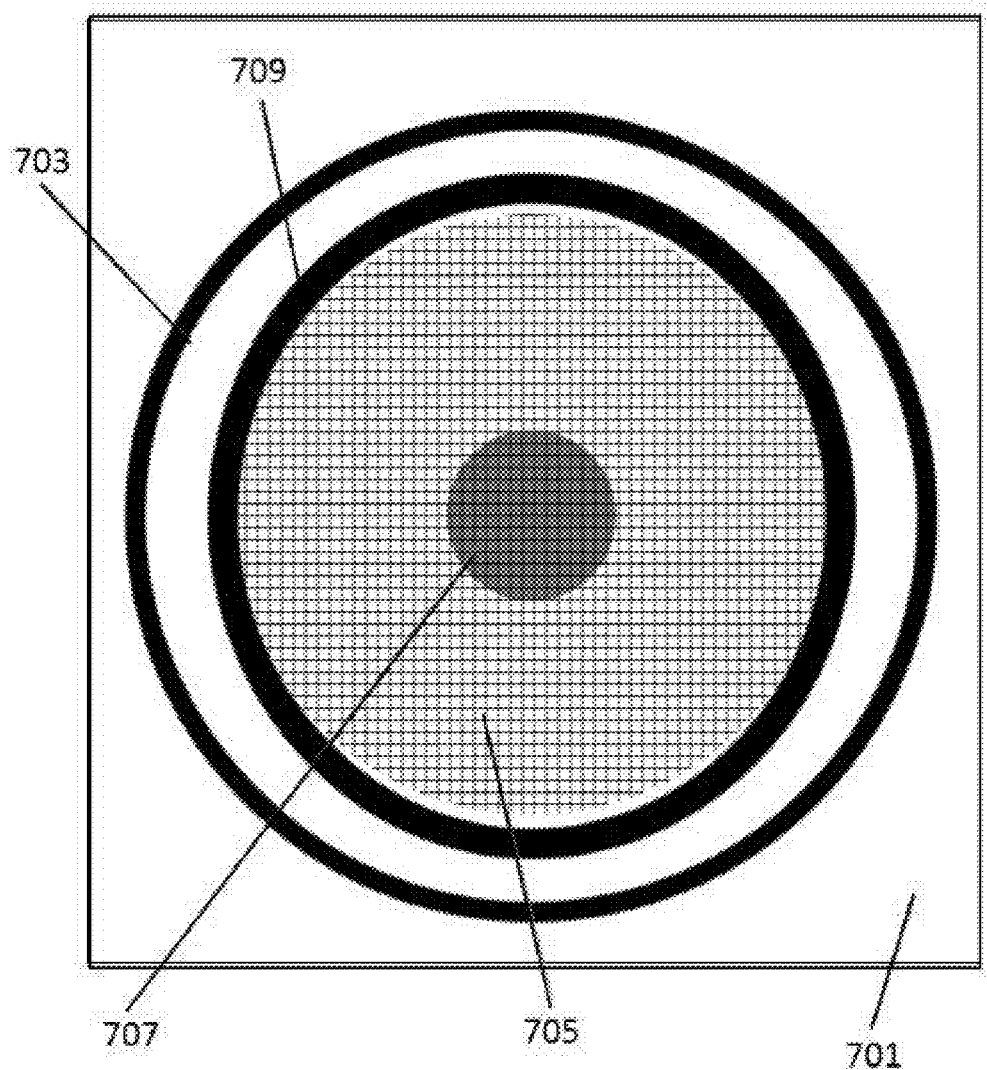
FIG. 39A shows a top perspective view of a sensor with a liquid ionophore coating which was formed using a surface tension dam approach.

FIG. 39A shows a top perspective view of a sensor with a liquid ionophore coating which was formed using a surface tension dam approach or Ring-Reference design. A circuit board or other substrate 701 includes a copper trace or other conductive material/circuit element 703, an ionophore or any material applied using a liquid deposition method 705, copper or other conductive material 707, and a soldermask, printed ink, or any other non-conductive material dissimilar to the circuit board printed, deposited to, or otherwise adhered to the circuit board prior to liquid deposition 709. The ionophore 705 preferably covers the copper or other conductive material 707.

Figure 39B:
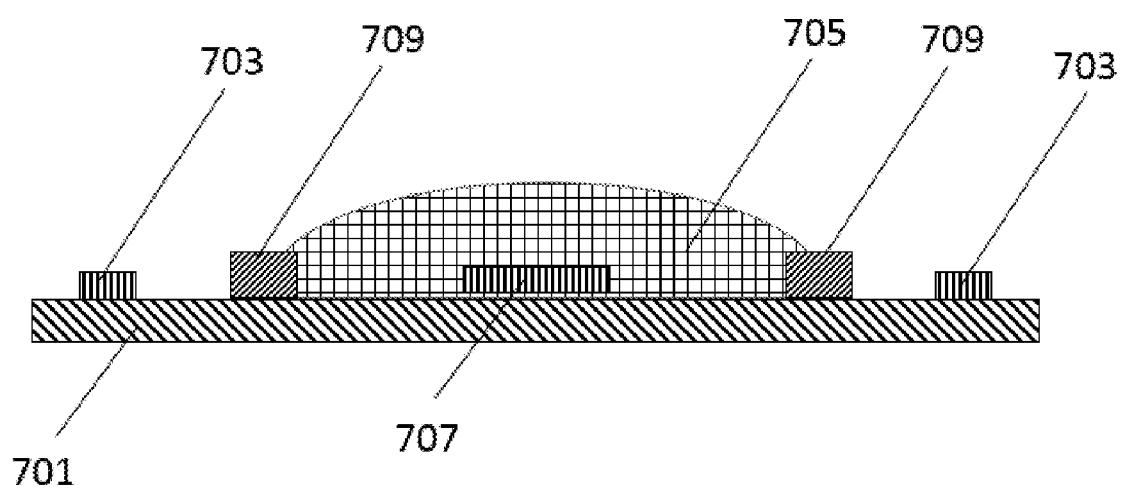
FIG. 39B shows a side perspective view of a sensor with a liquid ionophore coating which was formed using a surface tension dam approach.

FIG. 39B shows a side perspective view of a sensor with a liquid ionophore coating which was formed using a surface tension dam approach or Ring-Reference design.

In another embodiment, a surface tension management solution includes a printed or screened non-conductive ring inside a ring electrode to create a surface tension discontinuity. A soldermask preferably is a surface tension discontinuity in the surface tension management solution. In another embodiment, printed ink is a surface tension discontinuity in the surface tension management solution. Printed ink refers to any printed, screened, or deposited non-conductive material. This surface tension discontinuity supports the uniform deposition of liquid ionophores. In another embodiment, a well design is utilized for the sensor head for ionophore and electrode isolation. Specifically, the well design mitigates the stretch and/or sliding issues by increasing abrasion resistance.

Figure 38A:
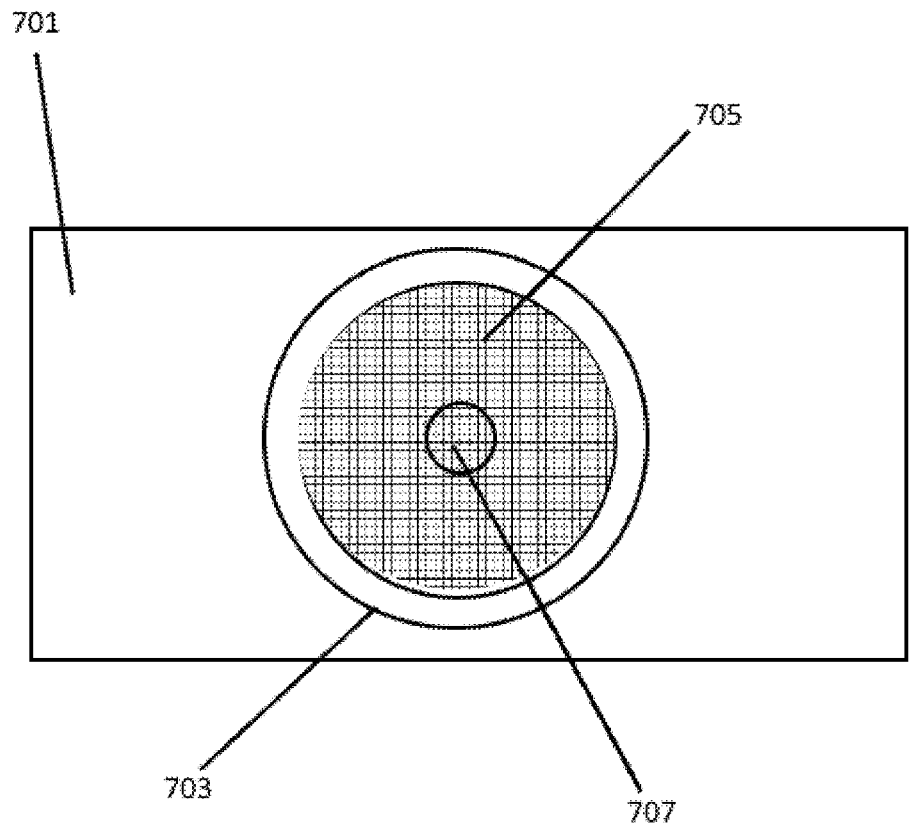
FIG. 38A shows a top perspective view of a sensor with a liquid ionophore coating which was formed using a well approach.

FIG. 38A shows a top perspective view of a sensor with a liquid ionophore coating which was formed using a well approach. A circuit board or other substrate 701 includes a copper trace or other conductive material/circuit element 703, an ionophore or any material applied using a liquid deposition method 705, and copper or other conductive material 707. The ionophore 705 preferably covers the copper or other conductive material 707.

Figure 38B:
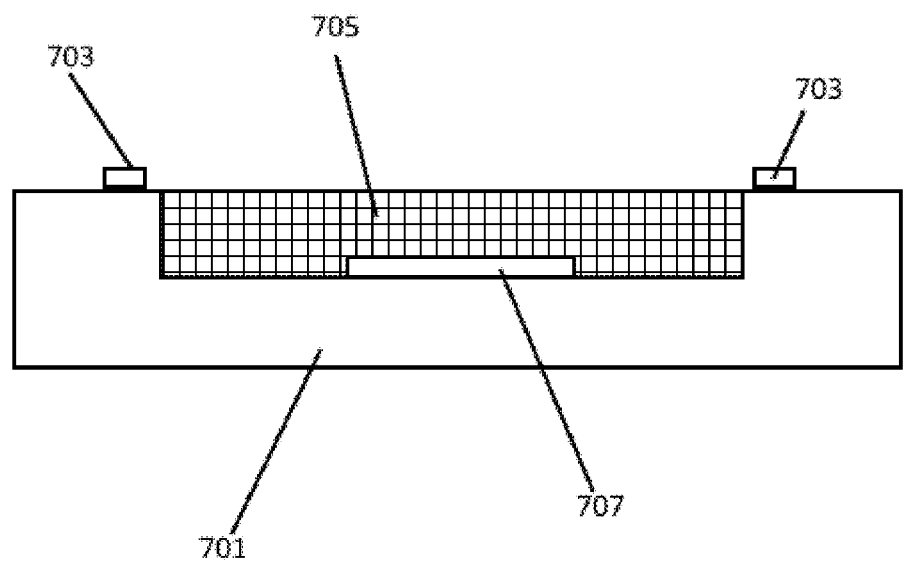
FIG. 38B shows a side perspective view of a sensor with a liquid ionophore coating which was formed using a well approach.

FIG. 38B shows a side perspective view of a sensor with a liquid ionophore coating which was formed using a well approach.

Figure 38C:
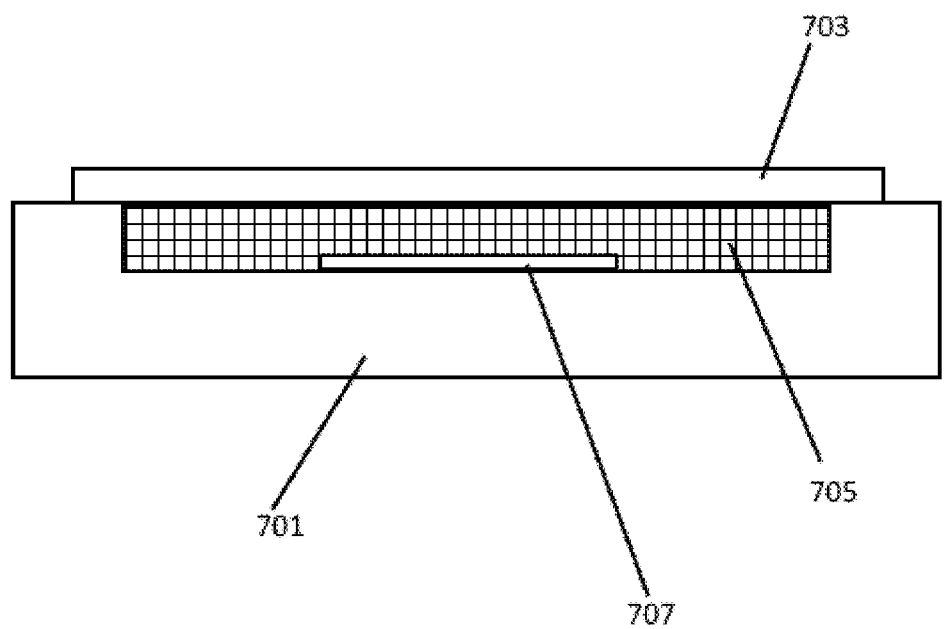
FIG. 38C shows another side perspective view of a sensor with a liquid ionophore coating which was formed using a well approach.

FIG. 38C shows another side perspective view of a sensor with a liquid ionophore coating which was formed using a well approach.

The Ring-Reference design or surface tension management solution and the well design are used to manage ionophore deposition, specifically liquid deposition on a surface. The liquid is preferably deposited on the surface of a circuit board and then solidifies and/or hardens.

Other variations in inter-sensor spacing are also utilized in the present invention. Variations in inter-sensor spacing improve sensor performance on a human-sensor interface. Specifically, closer spacing between sensors generally contributes to crosstalk and parasitics. The location and proximity of a reference sensor can also prevent issues for chemical, electrical, and mechanical isolation. Both chemical and mechanical interactions can compromise measurements of adjacent sensors, especially when sensors are of dissimilar construction and/or electrical specification. Preferably, the location of a chloride sensor relative to a sodium sensor and/or a potassium sensor is varied to increase abrasion resistance, which mitigates stretching and/or sliding issues. Preferably, the location of the chloride sensor is not proximal to the location of Na and K sensors to avoid chemical and mechanical interactions between the sensors.

The sensor also includes a galvanic skin response sensor in one embodiment. A longer lead and/or additional ground plane under the battery are preferably utilized to resolve complications resulting from adding a galvanic skin response sensor and/or a chlorine sensor.

In yet another embodiment, utilizing alternative flex substrates and conductor construction provides increase abrasion resistance. Preferably, silver ink on polyester or a material similar to polyester is utilized.

Preferably, the sensor of the present invention does not include a jumper or a Galvanic Skin Response (GSR). In one embodiment, FR4 is added under molex or directly integrated into the BR/uC and RF antenna.

The apparatus is also optimized for efficient and successful transmission during athletic usage. When the electrodes contact the sweat biomarkers a voltage is produced. Three electrodes per analyte are used to create an average voltage value, which is transmitted to the microcontroller, wherein the microcontroller pre-processes and prepares the sensor data to be communicated to the transceiver device via Bluetooth communication in preferred embodiments. Alternatively, an RFID, NFC, or other proprietary communications chip may be provided. The NFC chip preferably has an increased base signal amplitude for better processing and lower resolution as well as better concentration confidence and resolution. Bluetooth is preferred due to its low energy, ubiquity, and low cost. Most any Bluetooth enabled device can pair with another Bluetooth device within a given proximity, which affords more ubiquitous communication between the microcontroller and a transceiver device. The dynamic and automatic connections of Bluetooth allow for multiple microcontrollers to communicate with a single transceiver device, which, by way of example and not limitation, would provide for a team-based situation, wherein the sweat data of multiple athletes is communicated to a single coach or team database.

Another embodiment provides for utilizing NFC and/or onboard power for system control and operation, NFC and serial interfaces for data transport, external range extenders, and system integration.

Preferably, the systems and methods of the present invention are sensor agnostic, meaning that the systems and methods work with a variety of sensors. By way of example and not limitation, the systems and methods of the present invention work with multiple sensor head configurations, including variations in sensor count, single reference electrode sensors, multiple reference electrode sensors, a variety of analyte concentration, a variety of analyte sensitivity, a variety of input impedances, analog measurement conditioning, digital sampling, etc. Notably, variations in hardware and/or firmware designs provide for the sensor agnostic systems and methods of the present invention. An exemplary hardware implementation of a configurable sensor interface for multiple pinout permutations and variable analog buffering/signal conditioning supports existing and future sensor designs. Exemplary firmware designs for sensitivity and noise mitigation include, but are not limited to, variable input impedance, sampling intervals, settling time, and input switching designs. Additionally, addling a settling delay between readings also mitigates noise. One embodiment of a settling delay includes switching the multiplexer, waiting 10 mS, then taking a reading. Another embodiment for noise mitigation includes lowering the gain on the analog digital converter (ADC), which raises input impedance, to produce higher voltage levels. Adding both a settling delay and a lower ADC gain together significantly mitigate noise.

Utilizing non-adjacent channel switching on a multiplexer also reduces noise in the form of crosstalk and/or ghosting. Specifically, firmware methods for sensor switching and measurement times include non-adjacent multiplexer selection and sensor specific settling times from sensor selection to ADC sampling. Standard single chip multiplexers can experience adjacent channel crosstalk or 'ghosting' from large impedance changes that can manifest as noise or erroneous measurements. Firmware solutions to avoid direct adjacency in measurement selection can reduce these effects and improve measurement electronics performance. This is particularly important in low signal environments.

Complex sensor selection methods can propagate transition noise into the measurement electronics. The settling time constant for different sensor types and variations due to sensor-human interactions can present wide fluctuations that are hard to manage with filtering. Firmware controlled selection-to-measurement time delays can mitigate these effects. This can be implemented on a per sensor type basis for systems with dissimilar sensor types. As an example, a 'ring reference' ISE has more localized/uniform human contact behavior across the active sensor and its associated reference. In contrast, a 'single reference-multiple sensor' ISE can have widely differing human contact behavior due to the distributed physical placement of the single reference and the specific sensor heads.

The systems and methods of the present invention preferably enable end-to-end flow and processing using a patch, wherein the data is eventually transmitted to a device or to the cloud for data processing and analytics. The patch preferably includes electronics and firmware to properly buffer, amplify, and manage timing required to optimize patch functions. The firmware is preferably modularized to enable engineers to set designated variables, filters, noise thresholds, and other attributes needed to accommodate many different sensor types, modalities, sensitivities, and other characteristics.

The present invention also provides systems and methods for addressing fault detection and isolation, electromagnetic compatibility (EMC) detection, radiofrequency interference detection, mitigation and event handling, addition of encryption for data integrity, personally identifiable information (PII) protection, and communications security.

Figure 10:
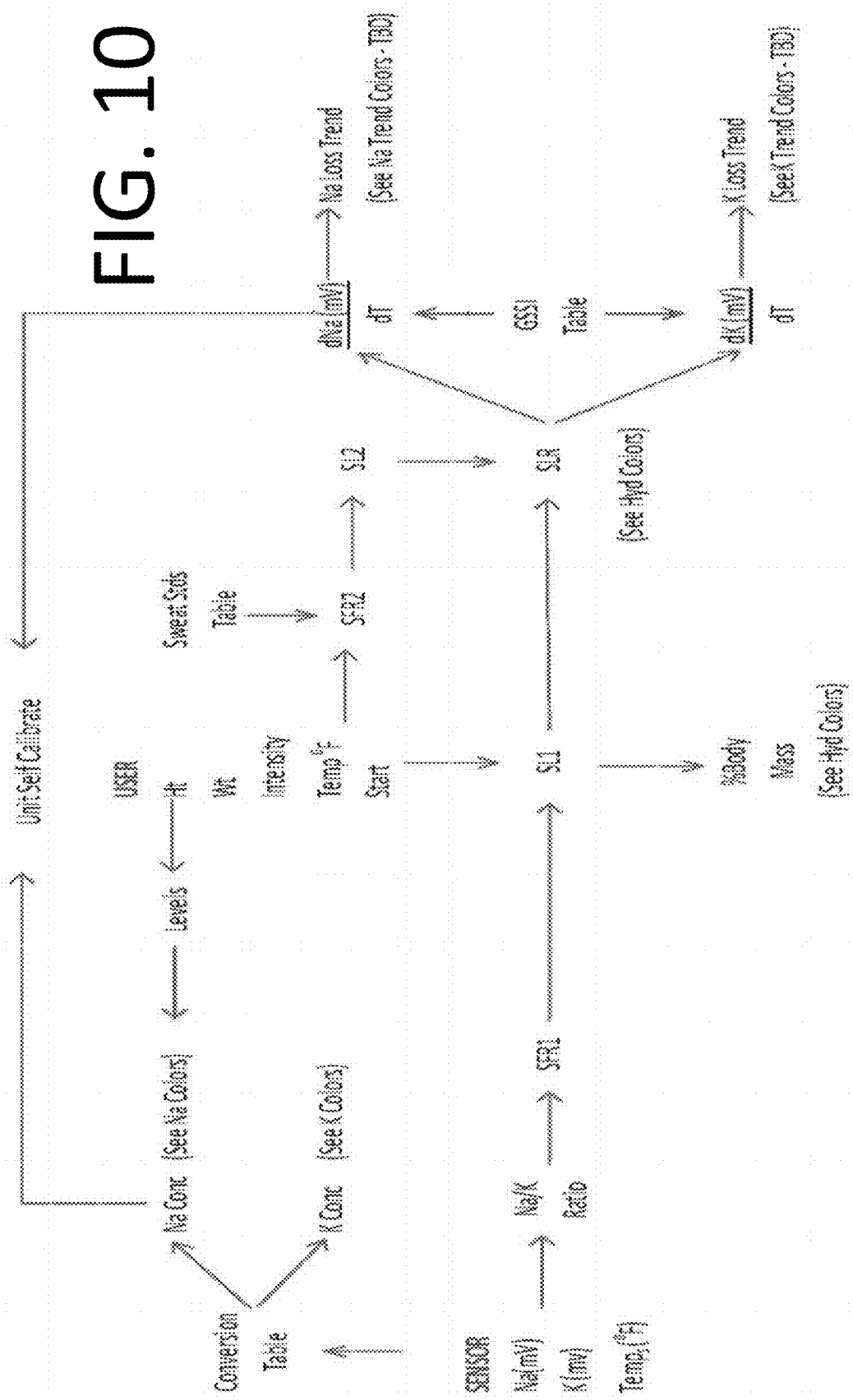
FIG. 10 shows a diagram of the analytical process within the sensor apparatus.
Figure 17:
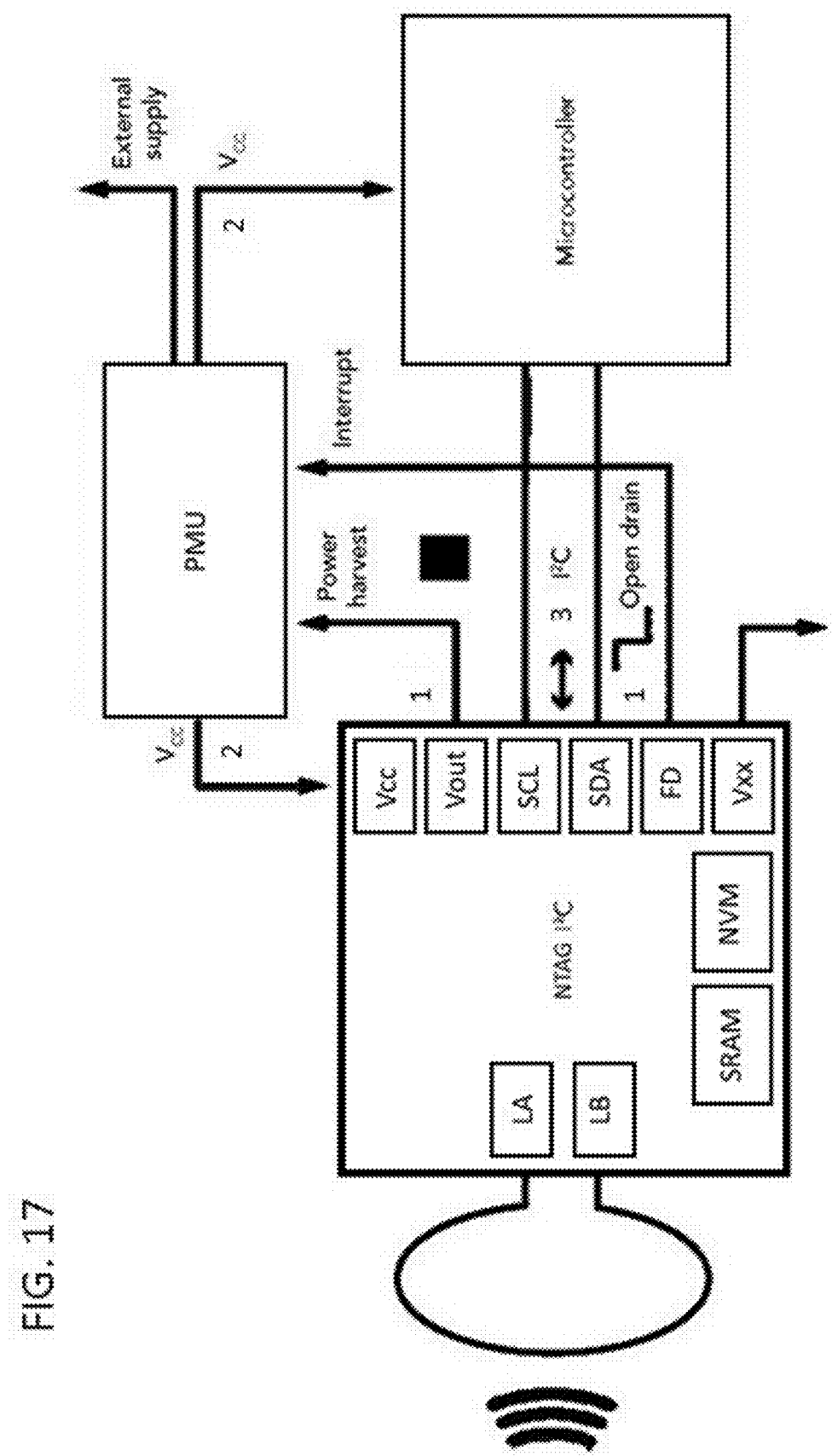
FIG. 17 shows a diagram of a NXP semiconductor used in an embodiment of the sensor apparatus.
Figure 18:
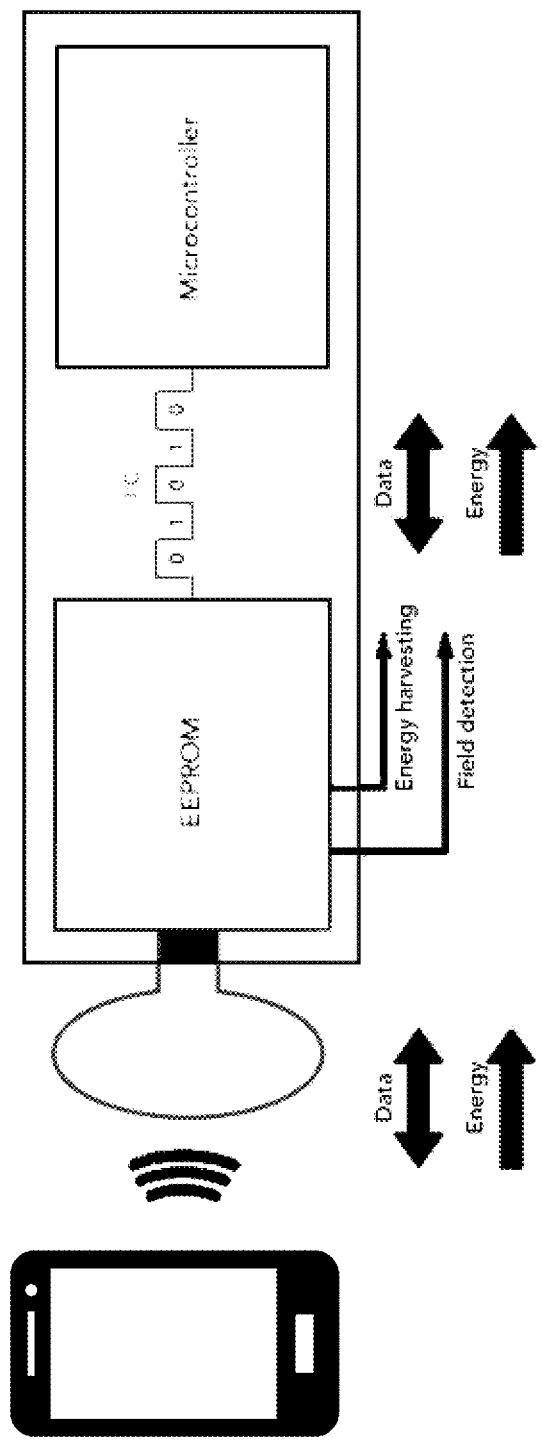
FIG. 18 shows a diagram of the communication between a NXP semiconductor and a wireless device in an embodiment of the sensor apparatus.
Figure 19:
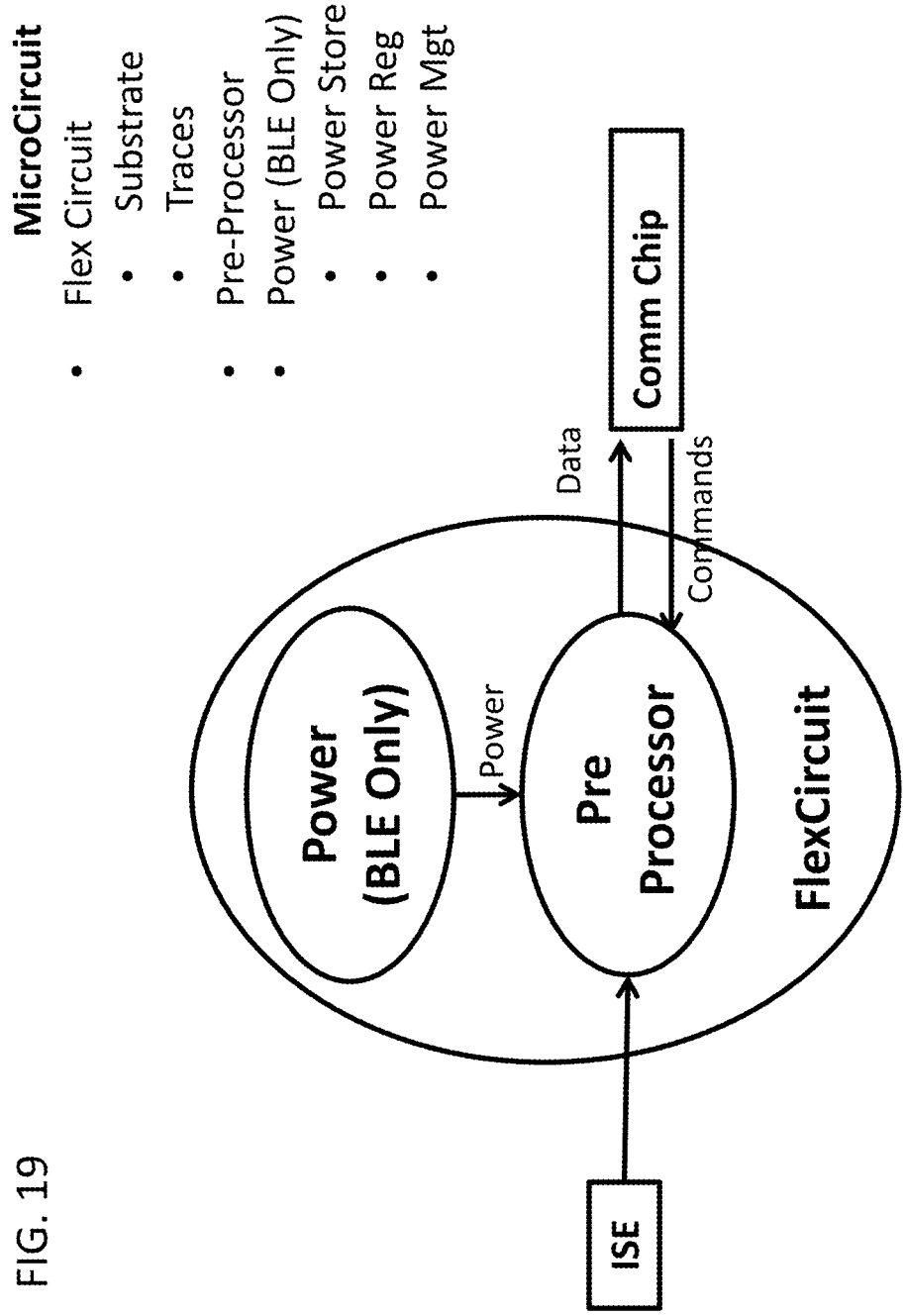
FIG. 19 shows a diagram of a sweat microcircuit of the sensor apparatus.

A second source of input data is the remote transceiver device. By two-way communication, the transceiver device may transmit data to the microcontroller of the apparatus, which is part of an inter-integrated circuit, as shown in FIGS. 17 and 18. The data to be transmitted will have been manually or automatically input in the transceiver device. For example and not limitation, as shown in FIG. 10, types of manually input data of the one or multiple users may include gender or gender factors, fitness or conditioning level, age, and anthropomorphic data, such as height and weight. The anthropomorphic data is preferably used to estimate user body surface area, which is a critical variable for accurately determining sweat loss and electrolyte loss. More preferably, estimates are a product of anthropomorphic data, gender, and age. Prior art assumes a body surface area of about 2 $m^2$ to calculate sweat loss and electrolyte loss. Using anthropomorphic variables, as in the present invention, consistently decreases calculated error rate from between about 50 and about 70 percent to less than about 10 percent, preferably. The accuracy resulting from body mass estimation revealed that persons with larger body mass, such as males, more readily adapt to physical exertion by sweating more quickly, a larger volume, and lower electrolyte concentration. Similarly, a physically fit person with a small body mass, such as a female, adapts to physical exertion by adjusting sweat flow rates and electrolyte levels. Although prior art has validly analyzed sodium, potassium, sweat rates, etc., it has failed to account for body surface area, mass, and VO2 max, thus inflating calculated error rate. These data support that sweat flow rates and electrolyte loss is strongly correlated with body size and surface area and conditioning level, which further supports the need for proper estimation of body size, such as through anthropomorphic variables.

Other types of manually input data include metabolic disorder, such as diabetes. Since Type 1 diabetes is associated with reduced eccrine gland activation and, thus, lower sweat rates, the present invention may reveal user metabolic disorder. Further, types of automatically input data include user skin temperature, outdoor or indoor temperature and/or humidity and altitude. This data is also input manually in another embodiment. Other automatically input data and/or manually input data includes exertion levels and/or body mass. The automatically input data may be generated in the remote transceiver device by integrated applications, such as GPS or weather. Together, the data transmitted to the microcontroller from the remote transceiver device represent modifying variables. Preferably, microcontroller software and/or software on the computing device is operable to compensate for variations across the automatically and/or manually input data.

Figure 11B:
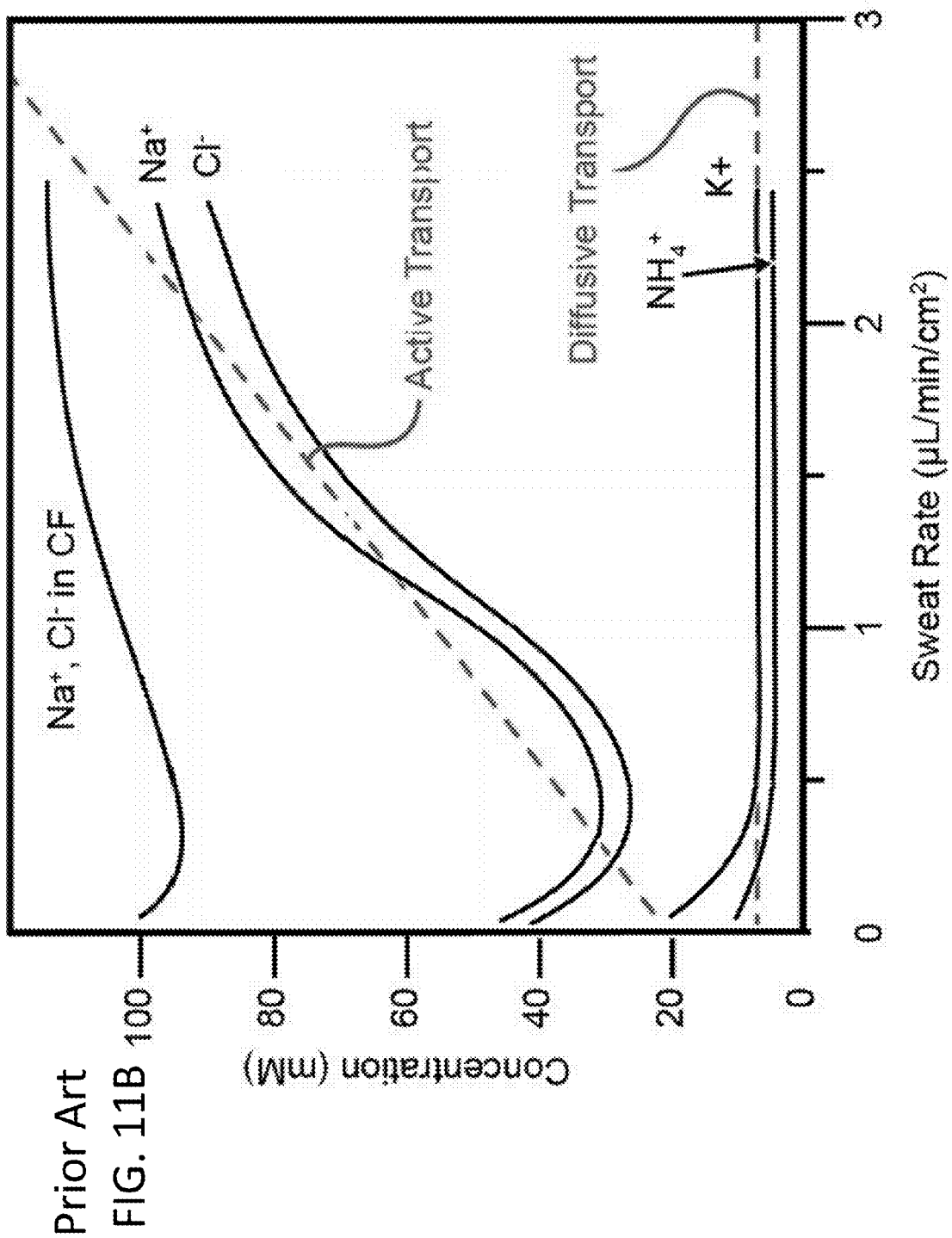
FIG. 11B shows a chart of concentration of ions vs. sweat rate.
Figure 12B:
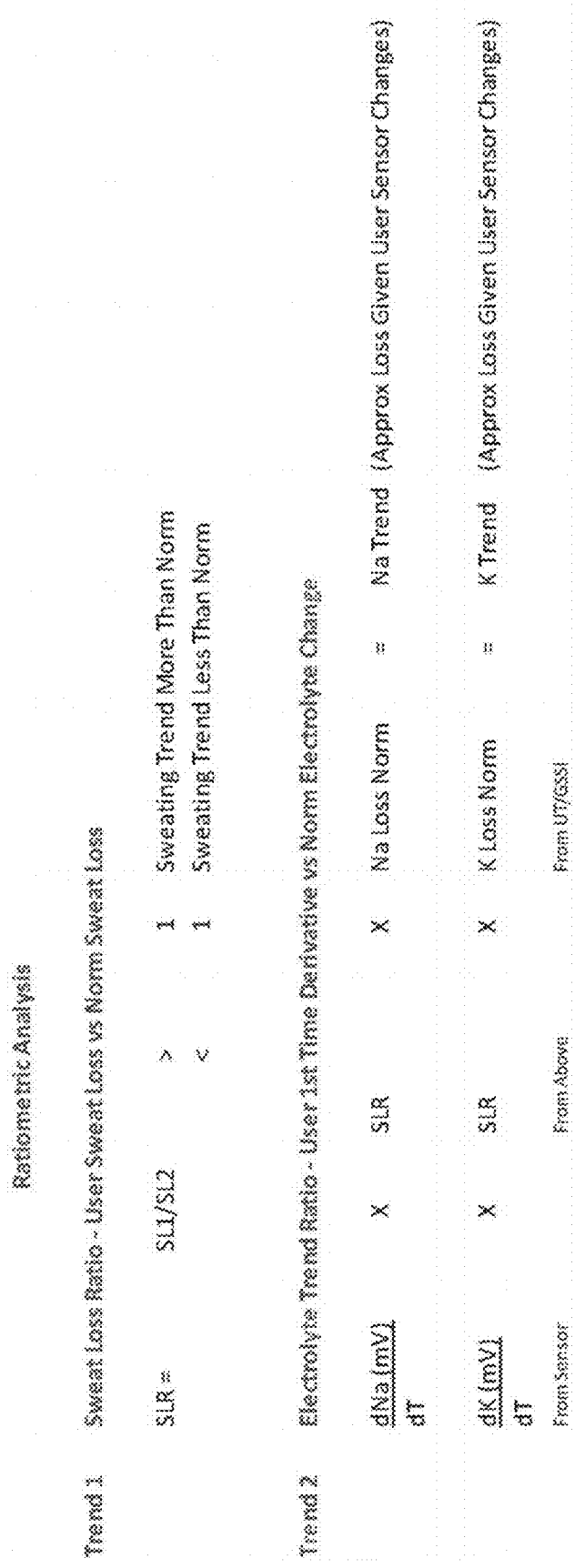
FIG. 12B shows a table of ratiometric analysis used within the sensor apparatus.
Figure 14:
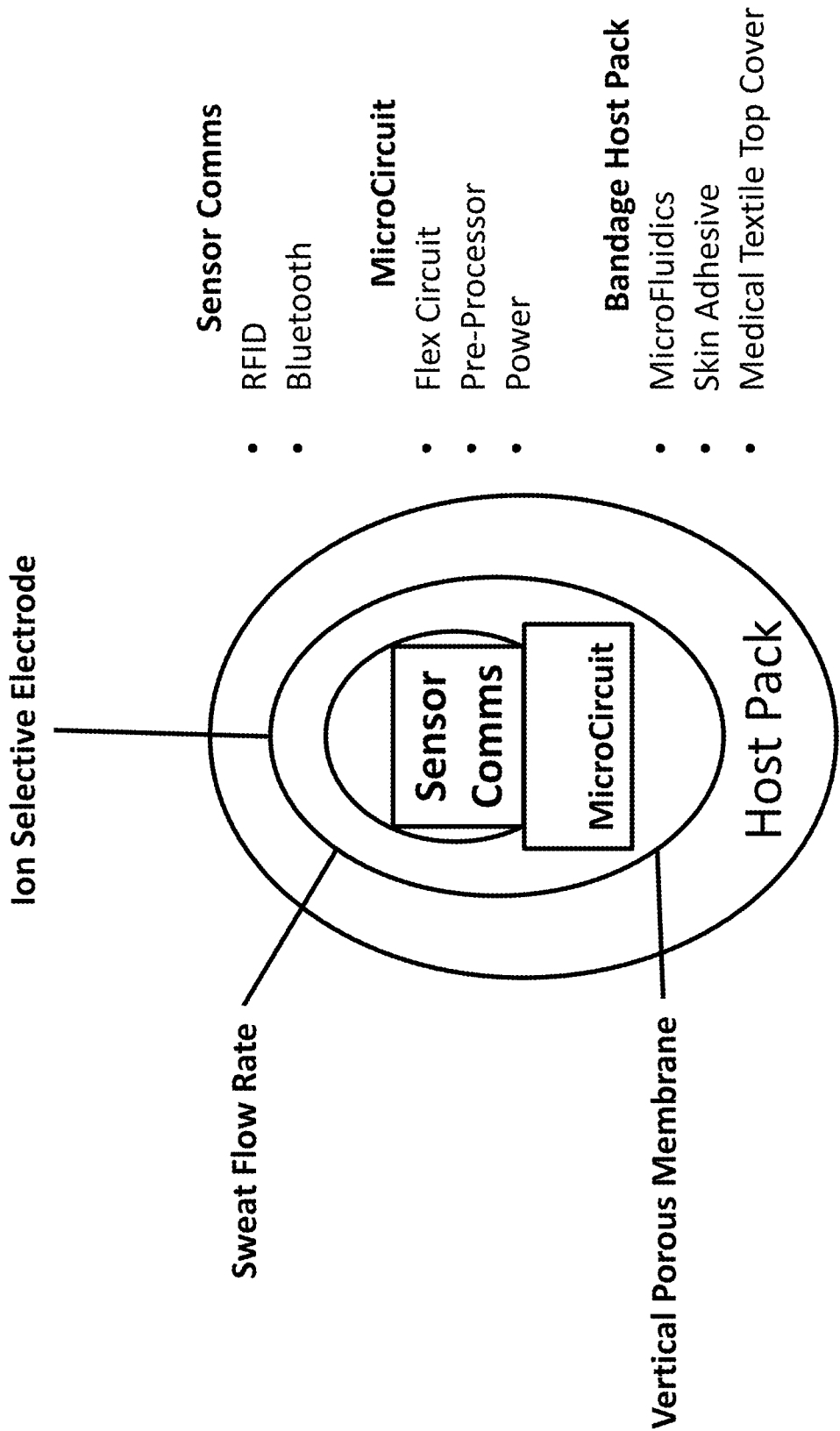
FIG. 14 shows a diagram of the sweat sensor subsystem.

The microcontroller converts the voltage data from the biological fluid into a concentration or ratio value of the biomarker using at least one programmed algorithm. For example, as shown in FIG. 11A, if the algorithm was converting the amount of sodium ions detected at the sensor into a sodium concentration, the algorithm would apply around 0.242 mM per mV of sodium. For potassium conversion, the ratio would be around 0.195 mM per mV of potassium. In one embodiment, sensor data are inputs into real time blood serum hydration, sodium concentration, and potassium concentration using absorption and extraction models that use sensor data as starting points. These calculated values are the apparatus' output data. Types of output data include but are not limited to concentrations, such as molarity, osmolarity, and osmolality, and descriptive statistics, such as averages, ratios, and trends, all of which may be categorized based on a sub-range within a larger physiological range of the biomarker, as shown in FIG. 13A. The modifying variables transmitted from the remote transceiver device may modify the algorithm, which may adjust the output data.

Figure 16:
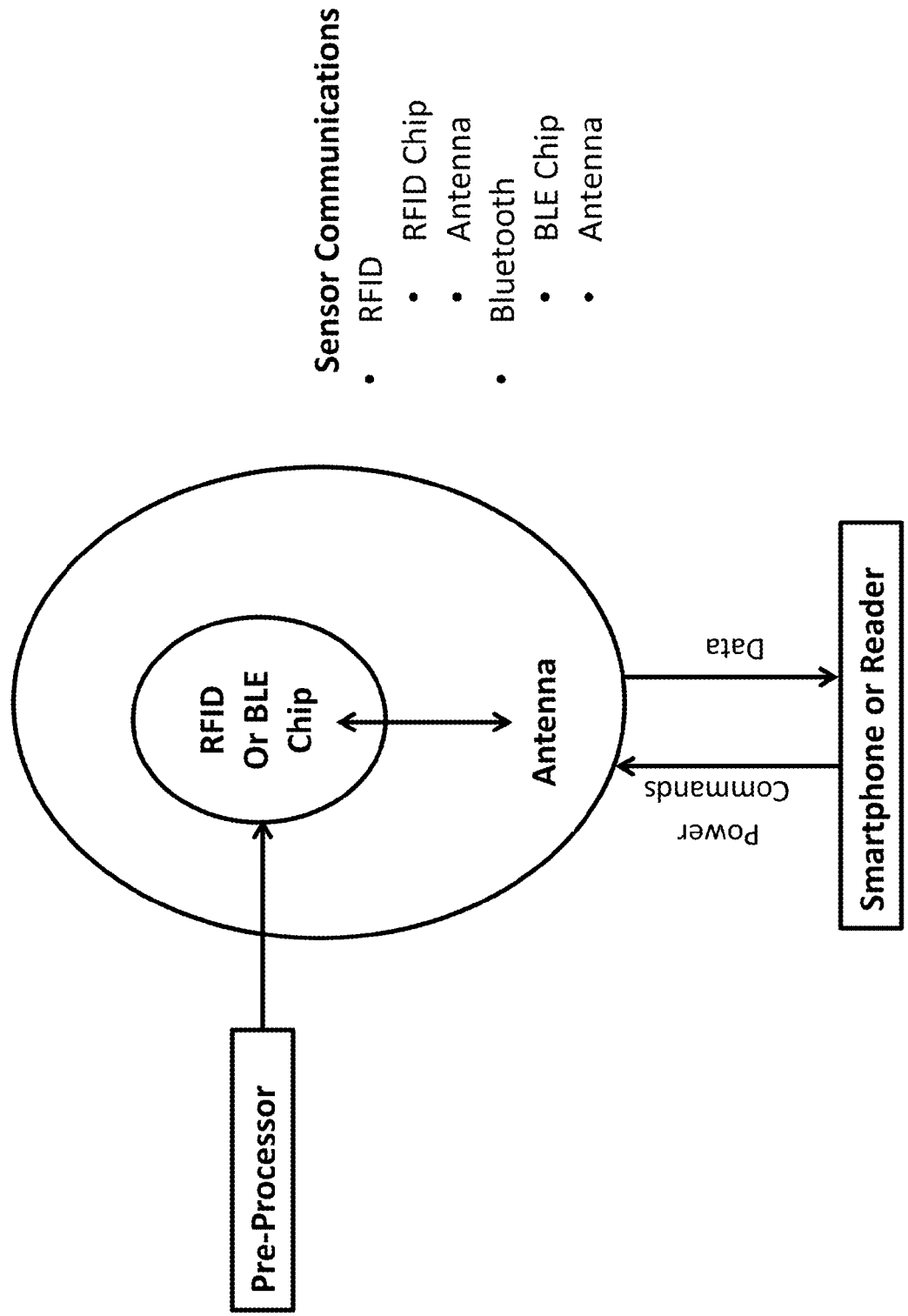
FIG. 16 shows a diagram of sweat sensor communications.

The output data is then transmitted from the apparatus to a remote computer device, such as by way of example and not limitation, a smartphone, a tablet computer, or wearable computer, preferably, through wireless network communication by the transceiver antenna (which may include a coil) of the apparatus. Using a larger antenna in the present invention provided for lower data loss and easier reads associated with a broad x-y placement tolerance. The wireless transmission is provided by any suitable wireless communication, wireless network communication, standards-based or non-standards-based, by way of example and not limitation, Bluetooth, radiofrequency, zigbee, near field communication, or other similar commercially utilized standards. At the remote transceiver device, the output data can be viewed and assessed by the one or multiple users. The one or more users also may manipulate or further analyze the output data, such as by creating user defined graphs and tables. Preferably, the remote transceiver device is portable. More preferably, the device is a smartphone. Alternative devices include bulk readers, such as food and or beverage dispensers with sensor and/or mobile app communication capabilities or athletic training gear including treadmills, spin bikes, ellipticals, stair climbers, and weight machines with integrated mobile communication capabilities. More alternative devices include desktop or laptop computers and tablets. FIG. 16 diagrams the communication between the sensor apparatus and the smartphone or reader, wherein power, commands, and/or data may be communicated.

From the remote transceiver device, the user may transmit processed or unprocessed data to at least one remote computer server, preferably by wireless communication, such as through a user web service. The remote computer server, which may be a network or cloud, may store the transmitted data in a library. The cloud preferably serves as a software development kit (SDK) for potential solution partners, a cloud based user app (with real time ingestion, calculation, and display), and a cloud based user store with ubiquitous access.

Figure 29:
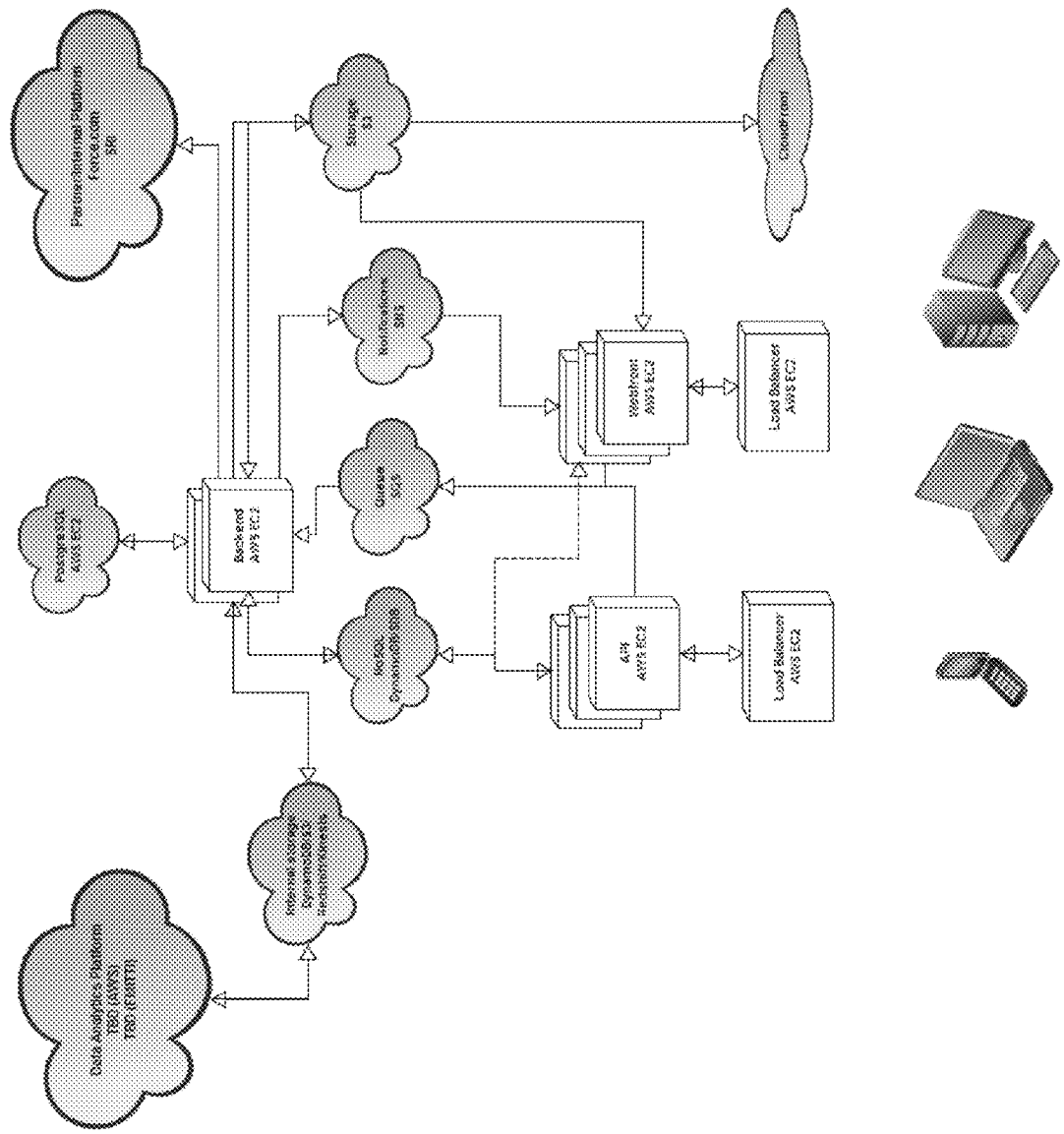
FIG. 29 shows a diagram of a cloud enterprise.

The library will include functions, such as file storage, security, extensions, utilities, scheduling, messaging, persistence, cache, and logging. FIG. 29 shows a cloud enterprise, wherein a cloud computing platform receives data from application users and processes it for internal and partner use. The software code that resides in a cloud-based computer system of the present invention is designed, constructed, and configured to handle the unique data in unique ways. It automatically validates data (to determine if it is reasonable/useable data) and triggers a series of workflows based on the type, date/time stamps, and scope of data to correlate and identify trends. It further includes correlation and trending tags for subsequent user alerts/analysis. The code has an open framework built on web service concepts to interact and integrate with other $3^{rd}$ party analytics. These web service calls are a series of open Application Programming Interfaces (APIs) aggregated into a Software Development Kit (SDK) which enables authorized $3^{rd}$ party developers to create and maintain $3^{rd}$ party user apps that leverage the cloud infrastructure to access/share data, correlations, trends, and other analytic results.

The two-way communication between the apparatus and the remote transceiver device is significant for the fullness of system functionality. As shown in FIG. 16, the remote transceiver device may communicate with the apparatus to provide, by way of example and not limitation, commands, electrode calibration, microcontroller software updates, new or updated algorithms, and/or new or updated modifying variables for algorithms. Communication may be manually or audibly activated. The apparatus may communicate with the remote transceiver device to provide, by way of example and not limitation, output data, microcontroller health properties, error codes, electrode maintenance or malfunction. At the transceiver device, the one or more users may separately or simultaneously view selected session tables, full history session tables, sensor or multi-sensor chronology, and external sensor correlation. Further, selected biomarker or multi-biomarker histories may be viewed.

Figure 20:
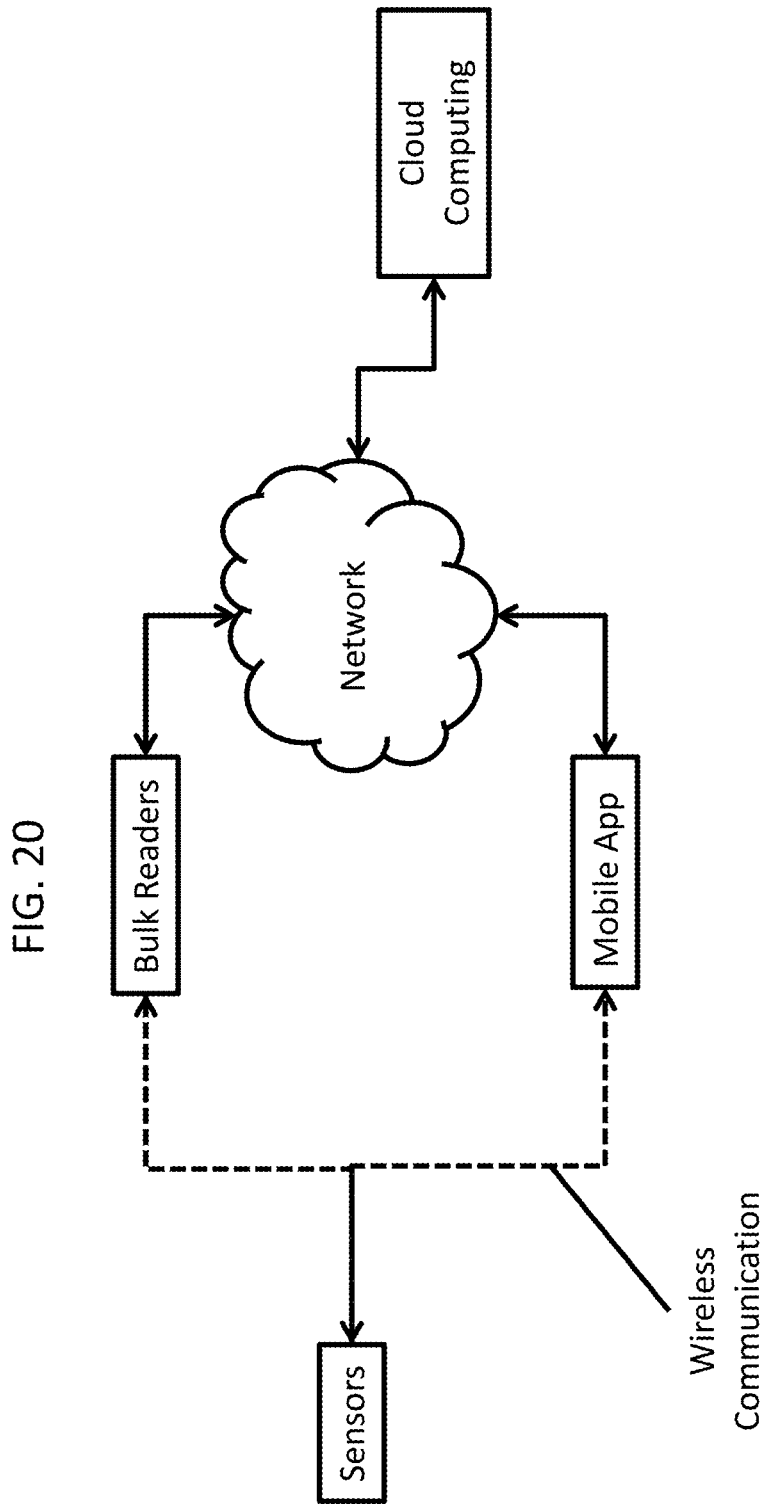
FIG. 20 shows a diagram of the system architecture.
Figure 21:
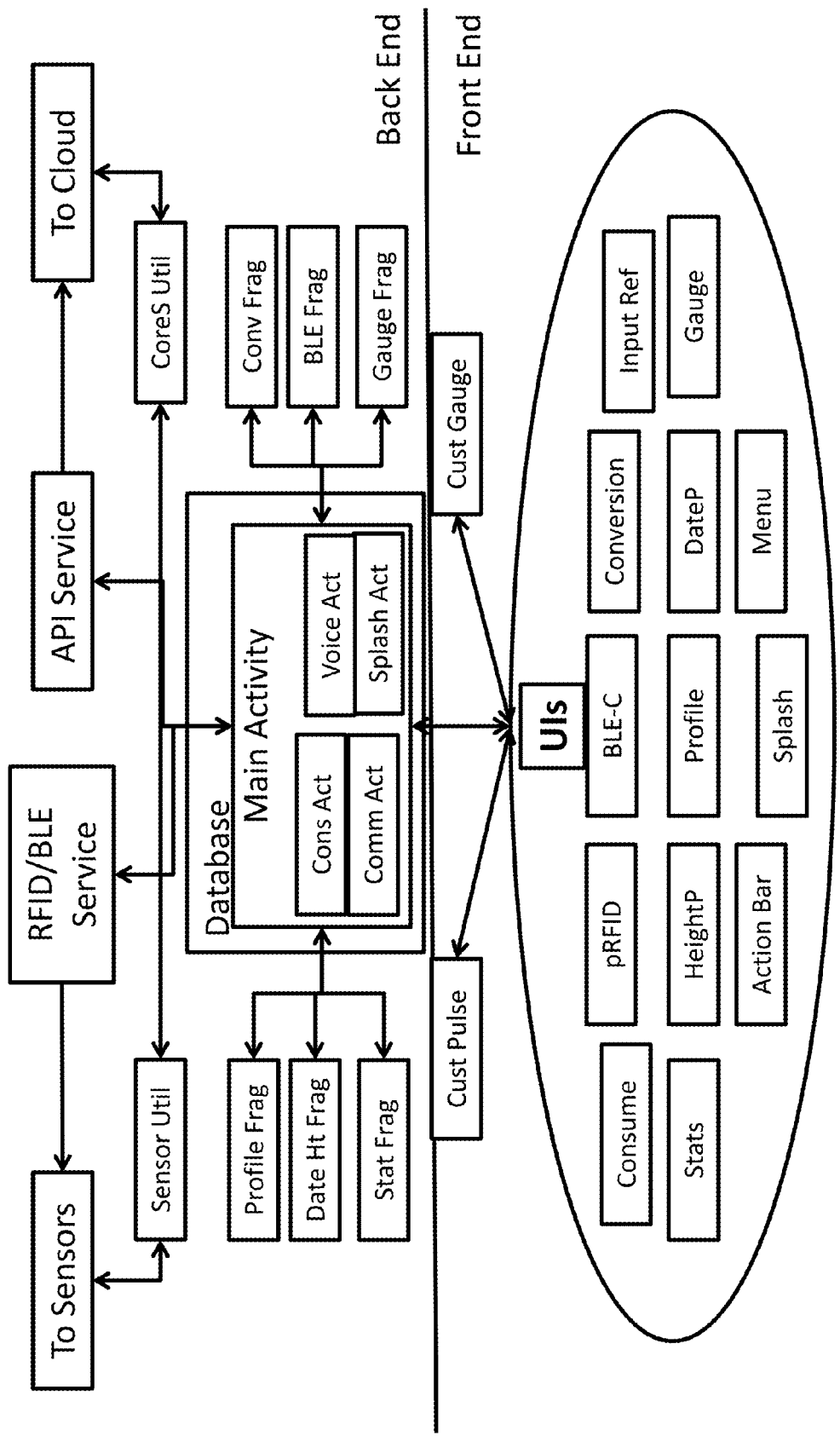
FIG. 21 shows a diagram of the controls within the user mobile app of the wireless remote transceiver.
Figure 22:
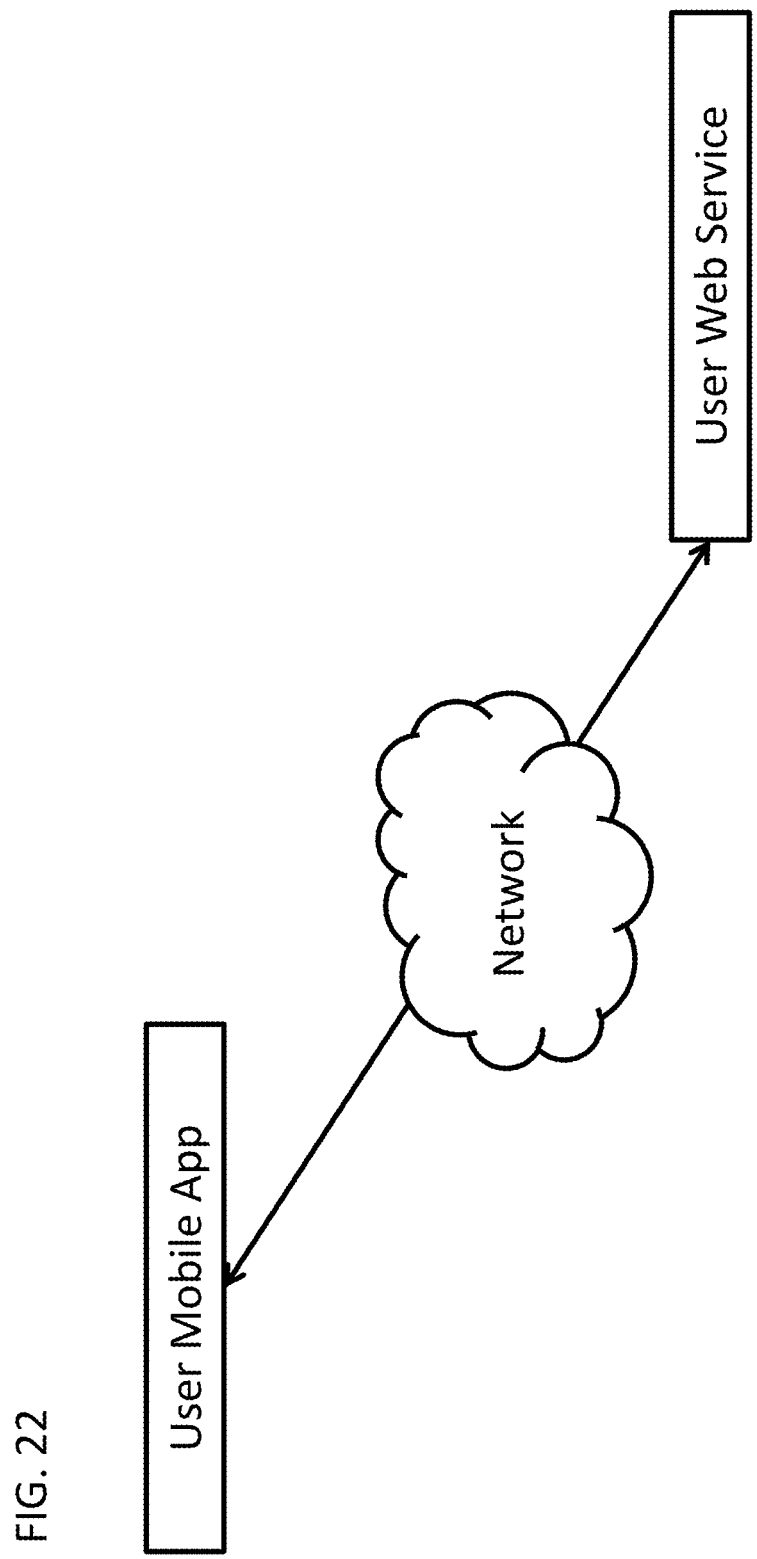
FIG. 22 shows a diagram of the network connection between the user mobile app and the user web service.
Figure 23:
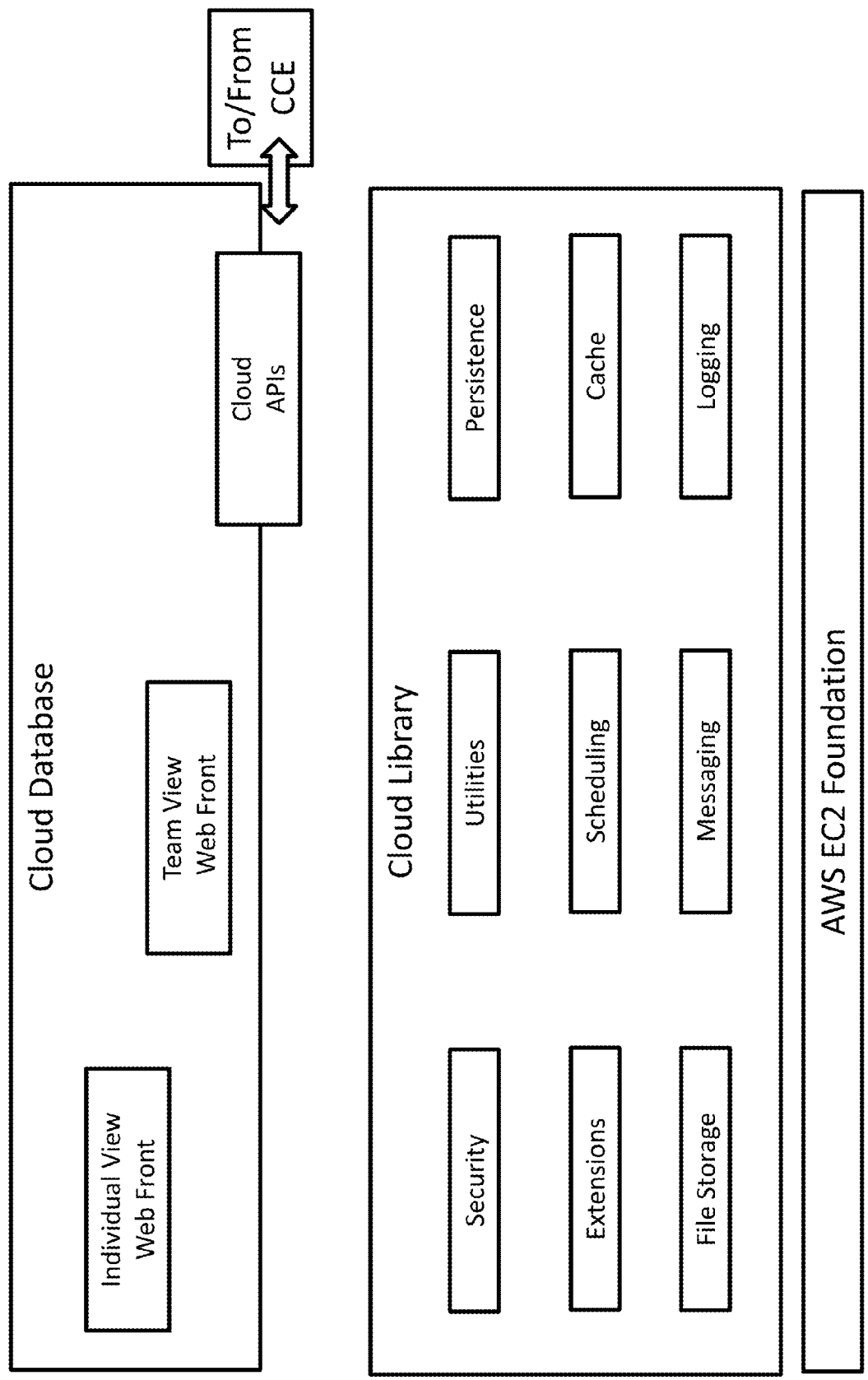
FIG. 23 shows a diagram of the controls within the cloud database and library, which are part of the user web service.
Figure 24:
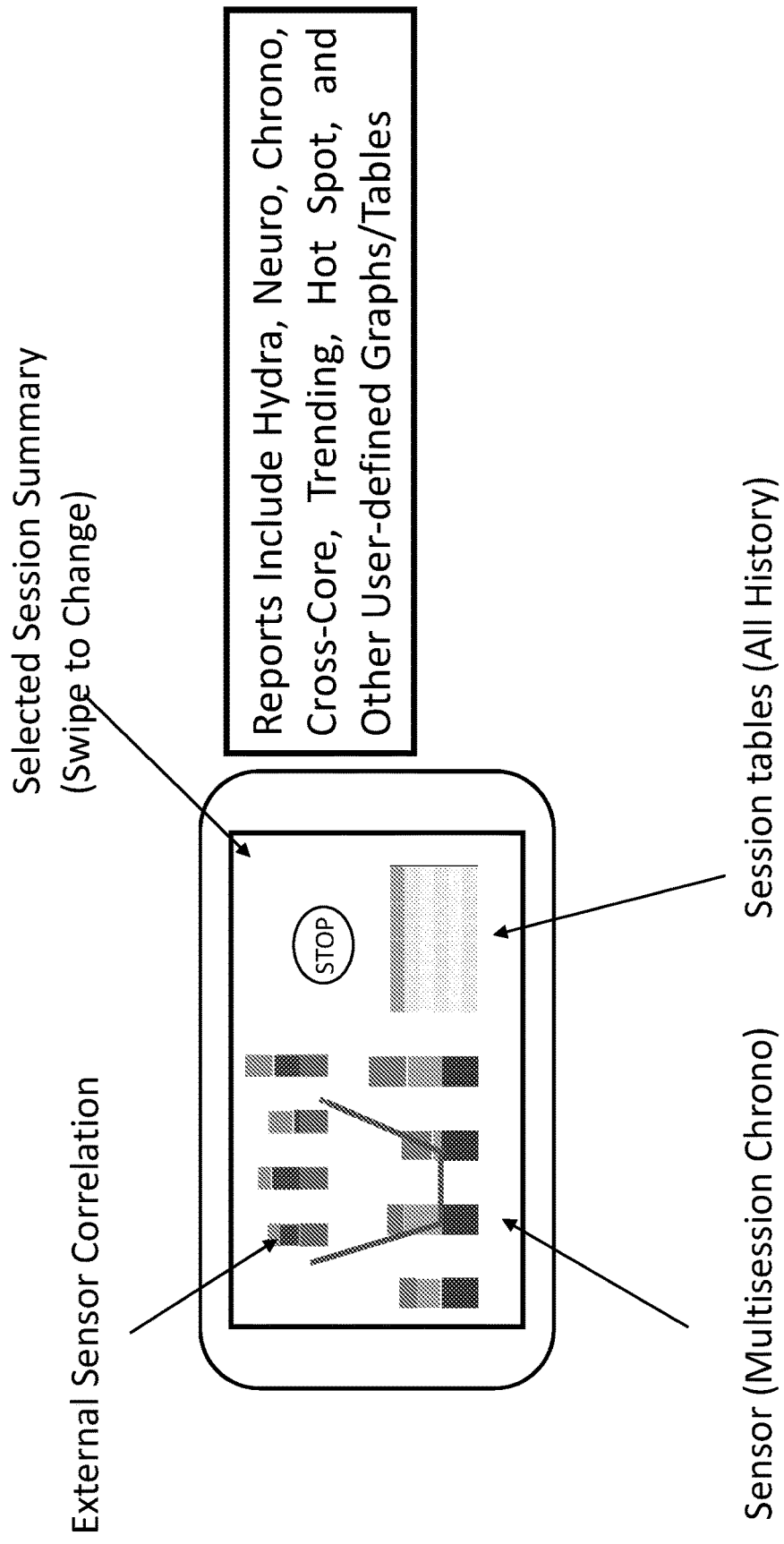
FIG. 24 shows an individual view of the user web front.
Figure 25:
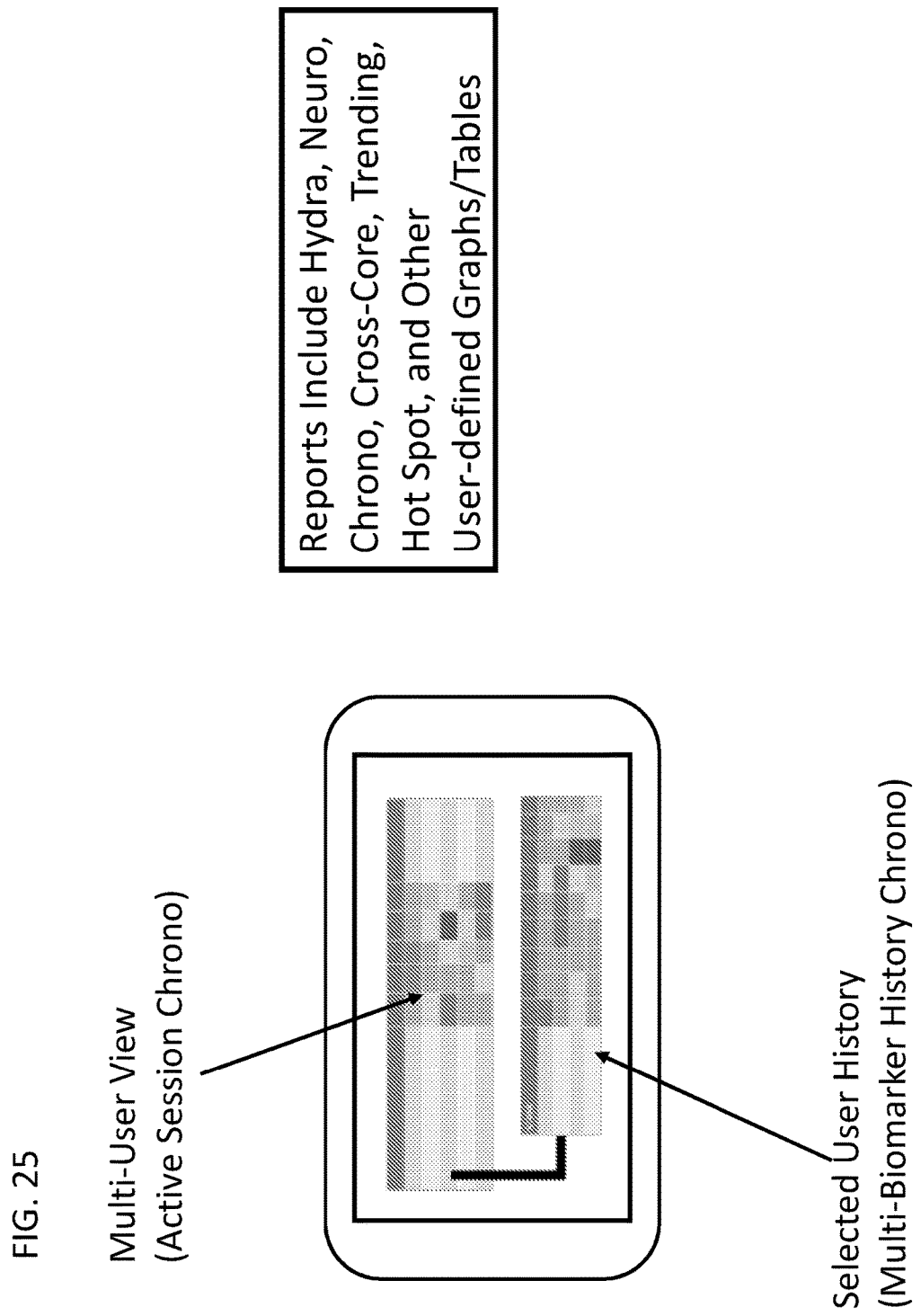
FIG. 25 shows a multi-user view of the user web front.
Figure 26:
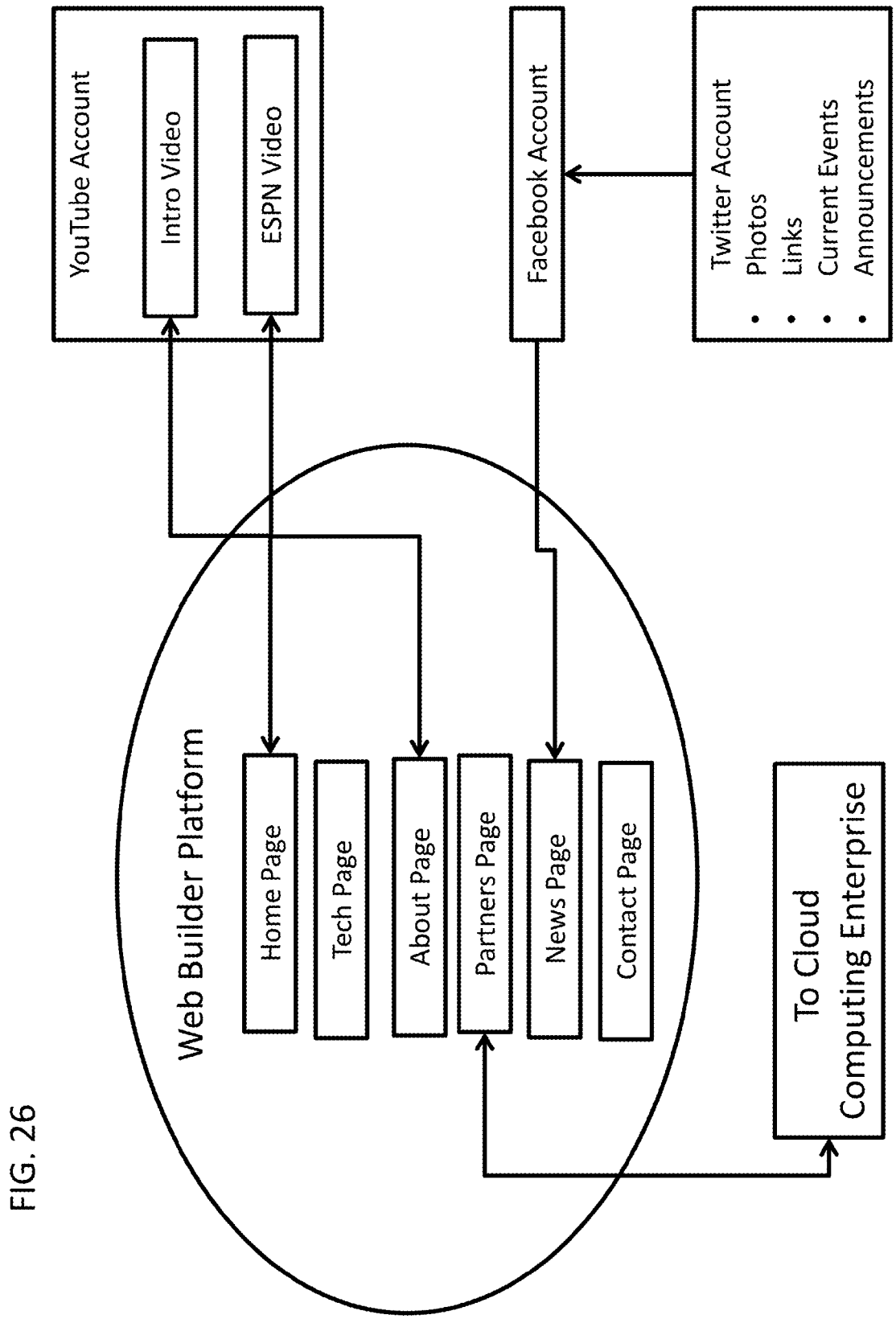
FIG. 26 shows a diagram of the controls within the present invention's website.
Figure 30:
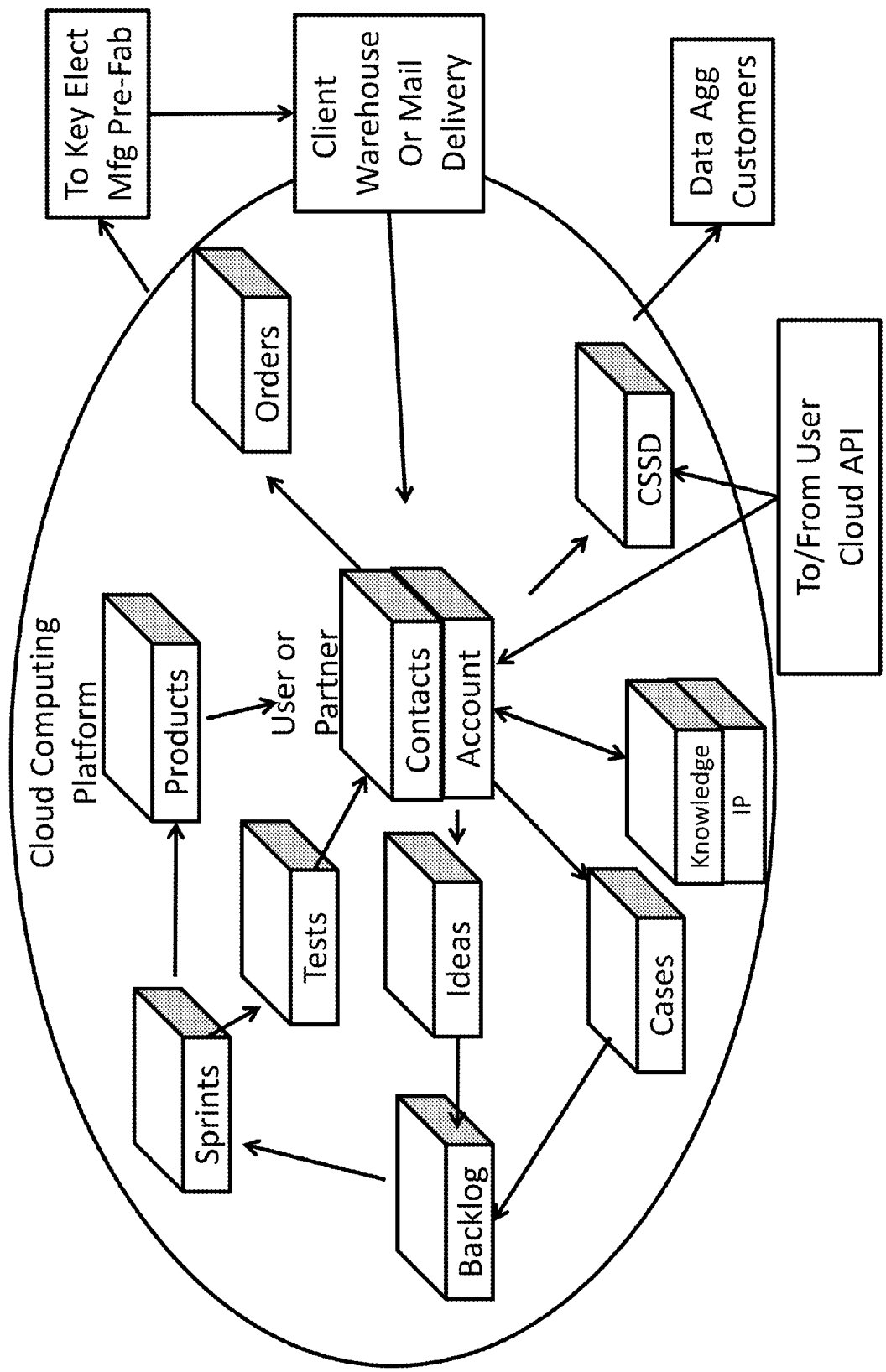
FIG. 30 shows a diagram of another embodiment of a cloud enterprise.

The system architecture is diagrammed in FIG. 20. Here, the remote transceiver device is characterized as a Mobile App, preferably on a smartphone, which is in communication with the sensor apparatus via wireless communication. Mobile App controls and commands are diagrammed in FIG. 21. The Mobile App may network with the user web service, as shown in FIG. 22, to access the cloud database and library, as shown in FIG. 23. An example cloud platform operable with the present invention is the EMITTI platform (ex: Amazon Web Services, Microsoft Azure, or any other similar commercial or private cloud platform); cloud architecture is more specifically detailed in FIG. 28. The web service allows the user to access, analyze, and manipulate user output data that was transmitted from the sensor apparatus. FIG. 24 shows an individual user web front including features such as external sensor correlation, selected session summary, and session tables. FIG. 25 shows the user web front for multiple users. The complete website builder platform is shown in FIG. 26. The website may connect to the cloud computing enterprise, which is diagrammed in FIGS. 29 and 30, or link to social media sites.

Figure 31:
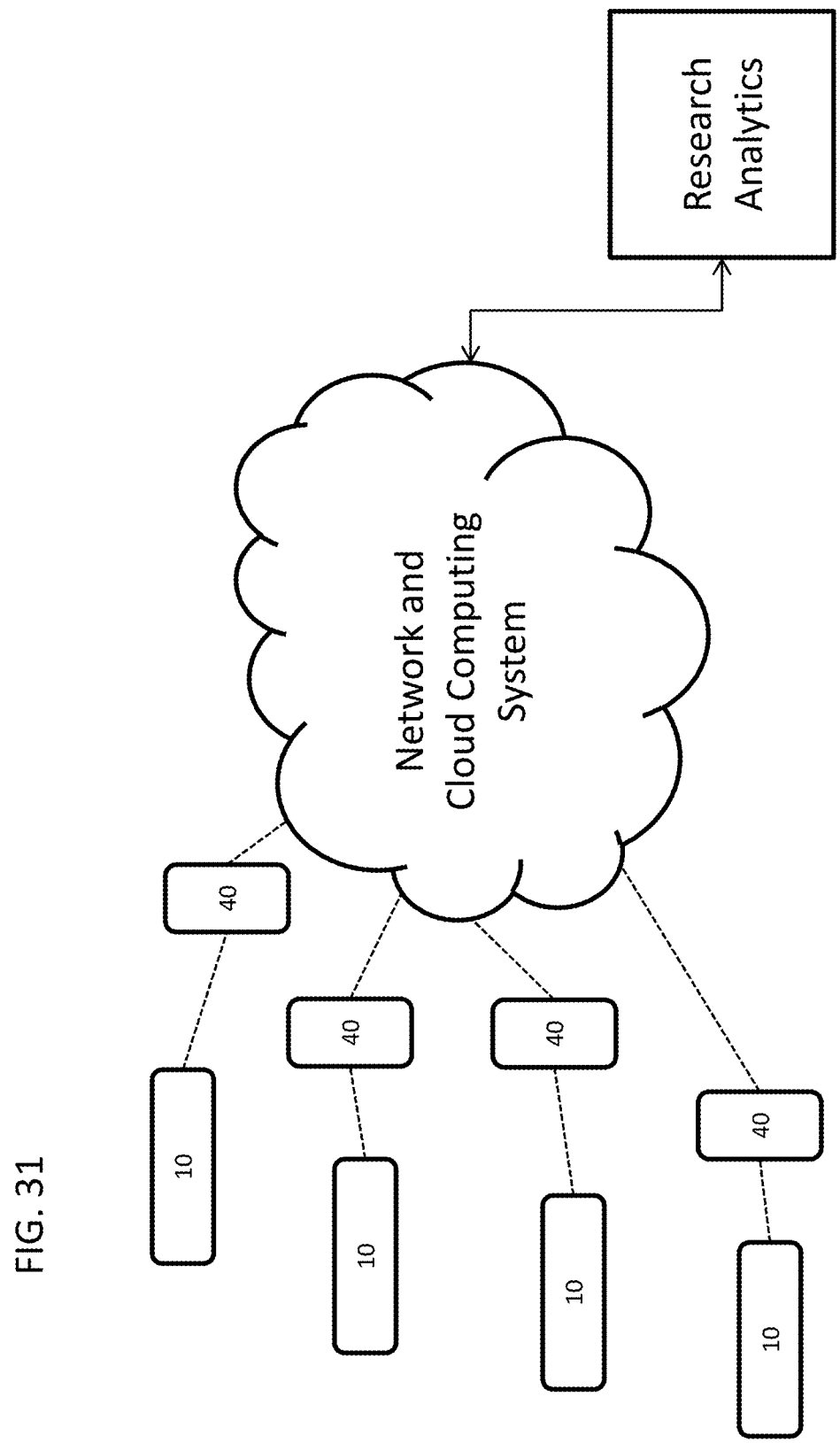
FIG. 31 shows a diagram of a system for epidemiological research.
Figure 32:
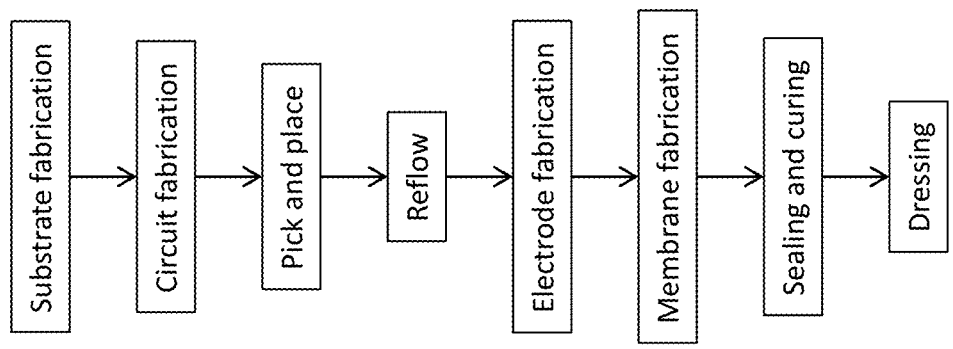
FIG. 32 shows a diagram of a manufacturing process for the sensor apparatus.

From the cloud computing system, data from multiple users may be stored, as diagrammed in FIG. 31. Access to these data may be acquired by researchers and epidemiologists to perform a variety of research analytics. The captured data will preferably be from the same sweat detection model, providing greater reliability to the pool of data. The ability to collect these specific biomarker data from such a large population of subjects creates an invaluable real-time, continuous epidemiological research system and method.

The preferred embodiment of the system includes an apparatus that intimately adheres to mammalian skin, more specifically to human skin. The sweat from the skin is moved into the apparatus for detection of sweat biomarkers and analytes. Where on the mammal the apparatus is positioned is dependent upon, by way of example and not limitation, user preference, sweat collection patterns, or sweat production amounts at a given location.

The apparatus is operable to determine a measured amount of transepidermal sweat and/or a measured amount of evaporative sweat and an estimated amount of transepidermal sweat and/or an estimated amount of evaporative sweat. In one embodiment, estimated amounts are determined based on body surface area, mass, gender, fitness level, weight, and/or age. In another embodiment, the apparatus is operable to compare the estimated amount of transepidermal sweat and/or the estimated amount of evaporative sweat to the measured amount of transepidermal sweat and/or the measured amount of evaporative sweat and provide a status based on the comparison of the estimated amount of transepidermal sweat and/or the estimate amount of evaporative sweat to the measured amount of transepidermal sweat and/or the measured amount of evaporative sweat. In another embodiment, the apparatus uses a tangible/quantifiable fitness level in combination with sweat biomarker ratios in order to calculate real-time sweat rates. In another embodiment, the apparatus uses gender factors in order to improve sweat flow rate accuracy. In another embodiment, the apparatus uses consumption refresh models, exact custom formula to return to start condition.

The apparatus is also operable to model losses and consumption of sweat in order to estimate blood serum characteristics at a time before use, at the start of use, in real-time, or at a time after use. In one embodiment, the apparatus is operable to predict performance erosion and injury probability based on the analysis of at least one biological fluid biomarker. In another embodiment, the apparatus is operable to use the analysis of sweat to provide corrective action recommendations.

Figure 33:
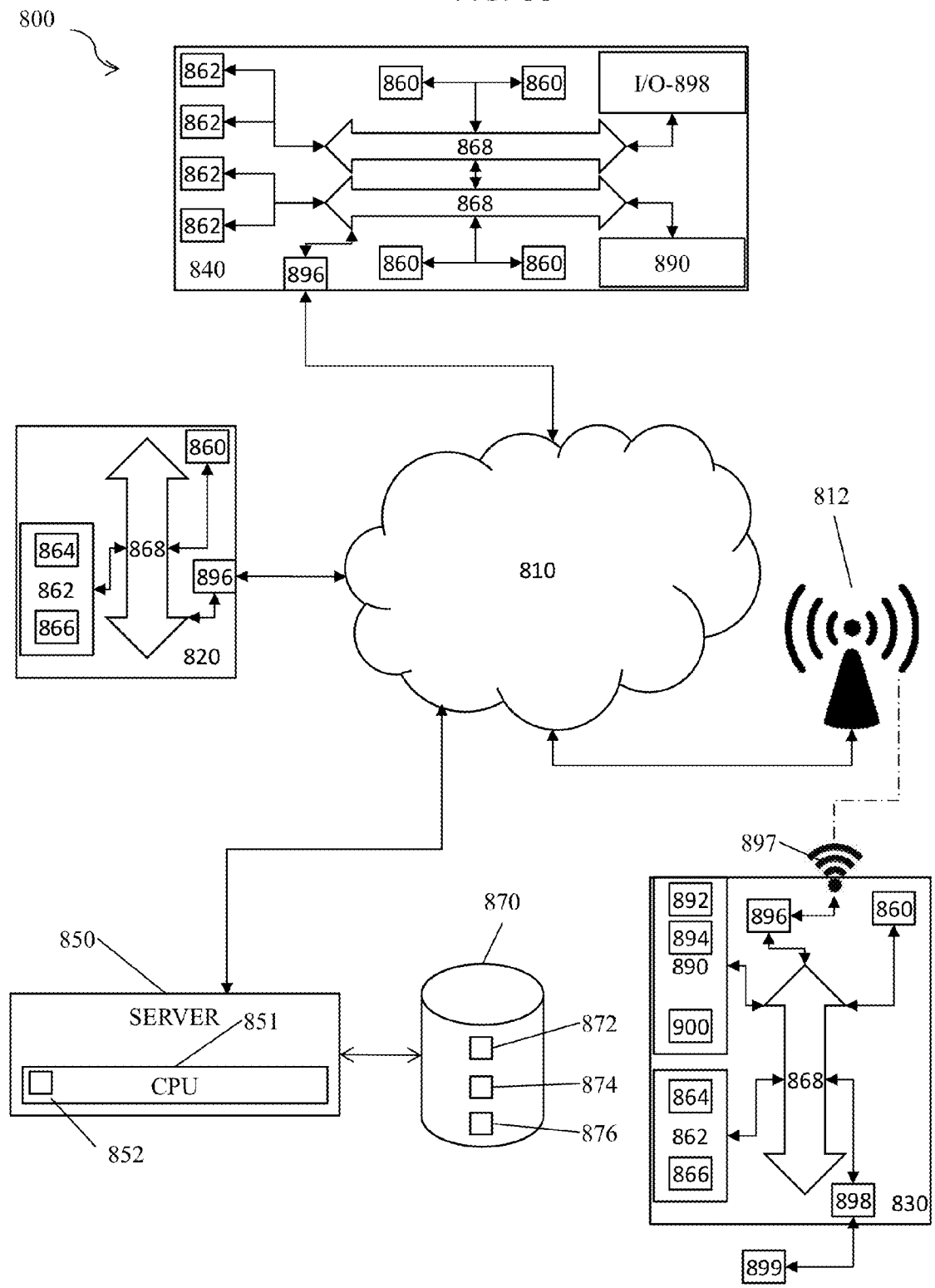
FIG. 33 shows a schematic diagram illustrating general components of a cloud-based computer system.

FIG. 33 is a schematic diagram of an embodiment of the invention illustrating a computer system, generally described as 800, having a network 810, a plurality of computing devices 820, 830, 840, a server 850 and a database 870.

The server 850 is constructed, configured and coupled to enable communication over a network 810 with a computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by a plurality of mobile communication computing devices 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, a personal digital assistant (PDA), a smart phone, a desktop computer, a netbook computer, a tablet computer, a workstation, a laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 33, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, disks or discs (e.g., digital versatile discs (DVD), HD-DVD, BLU-RAY, compact disc (CD), CD-ROM, floppy disk) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 33, may include other components that are not explicitly shown in FIG. 33, or may utilize an architecture completely different than that shown in FIG. 33. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

By way of definition and description supporting the claimed subject matter, preferably, the present invention includes communication methodologies for transmitting data, data packets, messages or messaging via a communication layer. Wireless communications over a network are preferred. Correspondingly, and consistent with the communication methodologies for transmitting data or messaging according to the present invention, as used throughout this specification, figures and claims, wireless communication is provided by any reasonable protocol or approach, by way of example and not limitation, Bluetooth, Wi-Fi, cellular, zigbee, near field communication, or other similar commercially utilized standards; the term "ZigBee" refers to any wireless communication protocol adopted by the Institute of Electronics & Electrical Engineers (IEEE) according to standard 802.15.4 or any successor standard(s), the term "Wi-Fi" refers to any communication protocol adopted by the IEEE under standard 802.11 or any successor standard(s), the term "WiMax" refers to any communication protocol adopted by the IEEE under standard 802.16 or any successor standard(s), and the term "Bluetooth" refers to any short-range communication protocol implementing IEEE standard 802.15.1 or any successor standard(s). Additionally or alternatively to WiMax, other communications protocols may be used, including but not limited to a "1G" wireless protocol such as analog wireless transmission, first generation standards based (IEEE, ITU or other recognized world communications standard), a "2G" standards based protocol such as "EDGE or CDMA 2000 also known as 1XRTT", a 3G based standard such as "High Speed Packet Access (HSPA) or Evolution for Data Only (EVDO), any accepted 4G standard such as "IEEE, ITU standards that include WiMax, Long Term Evolution "LTE" and its derivative standards, any Ethernet solution wireless or wired, or any proprietary wireless or power line carrier standards that communicate to a client device or any controllable device that sends and receives an IP based message. The term "High Speed Packet Data Access (HSPA)" refers to any communication protocol adopted by the International Telecommunication Union (ITU) or another mobile telecommunications standards body referring to the evolution of the Global System for Mobile Communications (GSM) standard beyond its third generation Universal Mobile Telecommunications System (UMTS) protocols. The term "Long Term Evolution (LTE)" refers to any communication protocol adopted by the ITU or another mobile telecommunications standards body referring to the evolution of GSM-based networks to voice, video and data standards anticipated to be replacement protocols for HSPA. The term "Code Division Multiple Access (CDMA) Evolution Date-Optimized (EVDO) Revision A (CDMA EVDO Rev. A)" refers to the communication protocol adopted by the ITU under standard number TIA-856 Rev. A.

It will be appreciated that embodiments of the invention described herein may be comprised of one or more conventional processors and unique stored program instructions that control the one or more processors to implement, in conjunction with certain non-processor circuits, some, most, or all of the functions for the systems and methods as described herein. The non-processor circuits may include, but are not limited to, radio receivers, radio transmitters, antennas, modems, signal drivers, clock circuits, power source circuits, relays, current sensors, and user input devices. As such, these functions may be interpreted as steps of a method to distribute information and control signals between devices. Alternatively, some or all functions could be implemented by a state machine that has no stored program instructions, or in one or more application specific integrated circuits (ASICs), in which each function or some combinations of functions are implemented as custom logic. Of course, a combination of the two approaches could be used. Thus, methods and means for these functions have been described herein. Further, it is expected that one of ordinary skill in the art, notwithstanding possibly significant effort and many design choices motivated by, for example, available time, current technology, and economic considerations, when guided by the concepts and principles disclosed herein, will be readily capable of generating such software instructions, programs and integrated circuits (ICs), and appropriately arranging and functionally integrating such non-processor circuits, without undue experimentation.

Certain modifications and improvements will occur to those skilled in the art upon a reading of the foregoing description, by way of example, a device having at least one microprocessor for storing data may be operable in the device before data transmission. Another example includes other advanced sensors, as well as being incorporated into smart fabrics and protective wear. Advanced sensors include advanced sweat biomarkers, pulse rate breath rate, micro EKG, micro O2, picture log, voice log, voice translate, tissue safe X-ray and combinations thereof. Smart fabrics incorporate the present invention and include active heat/cooling, kinetic energy generation, electromagnetic energy harvesting, wearable energy storage, wearable data storage, wearable processing, wearable communications, elastomeric actuators, and combinations thereof. More generally, the apparatus may be part of apparel and material for clothing, wherein the clothing may be for lower body, like socks and athletic underwear, upper body, like shirts and forearm bands, or head, like stocking cap or headband. Specifically, sensors, conductors and/or ionophores are utilized on moisture management fabrics, such as by way of example and not limitation, Under Armour fabrics. Microfluidic moisture transport is also utilized in fabric and other material which directly contacts human skin when worn. The present invention is also incorporated into enhanced protective wear such as enhanced helmets, gloves and footwear. Enhanced helmets include those with MRI, 3D audio, visual enhancement, mixed reality, breath sensors, aerosol nutrition and combinations thereof. Enhanced gloves include touch communications, elastomeric grip, gesture control and combinations thereof. Enhanced footwear includes power generation boots, 3D tracking, tactile alerts, communication transceivers, and combinations thereof.

The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A system for analyzing sweat from a human and transmitting and storing sweat data from the human comprising:
 an apparatus for sensing and analyzing sweat, wherein the apparatus includes an electronic layer comprising at least one electrochemical sensor, a microcontroller, and a transceiver antenna coil;
 at least one remote transceiver device; and
 at least one remote computer server;
 wherein the apparatus analyzes at least one sweat biomarker, calculates at least one output datum of the at least one sweat biomarker using at least one algorithm, and transmits the at least one output datum to the at least one remote transceiver device;
 wherein the at least one algorithm calculates the at least one output datum using an estimated body surface area of a human and input data, wherein the input data includes at least a height and a weight of the human, and wherein the height and the weight of the human are used to estimate the estimated body surface area of the human;
 wherein the at least one remote transceiver device transmits the at least one output datum to the at least one remote computer server or at least one remote computing device or database for storage;
 wherein the apparatus and the at least one remote transceiver device have real-time or near-real-time two-way communication; and
 wherein the apparatus is flexible and further includes:
  a macrofluidic, double-sided adhesive layer;
  a microfluidic management layer; and
  a vapor porous, top protective layer;
 wherein the macrofluidic, double-sided adhesive layer is intimately adhered to an exterior layer of human skin;
 wherein the microfluidic management layer is positioned between the macrofluidic, double-sided adhesive layer and the electronic layer;
 wherein the microfluidic management layer circumferentially surrounds the at least one electrochemical sensor of the electronic layer;
 wherein the at least one electrochemical sensor of the electronic layer is facing the exterior layer of human skin;
 wherein the electronic layer is intimately adhered to the macrofluidic, double-sided adhesive layer;
 wherein the vapor porous, top protective layer is placed on and completely covers the microfluidic management layer and the electronic layer; and
 wherein the vapor porous, top protective layer is intimately adhered to the macrofluidic, double-sided adhesive layer.

2. The system of claim 1, wherein the at least one sweat biomarker includes small molecules, proteins, metabolites, and/or electrolytes.

3. The system of claim 1, wherein the microcontroller receives multiple input data, which are input from multiple sources including the sweat.

4. The system of claim 1, wherein the at least one electrochemical sensor houses at least one standard electrode and at least one active electrode.

5. The system of claim 4, wherein the at least one standard electrode and/or the at least one active electrode are silver, zinc, copper, gold, platinum, rhodium, carbon, or a combination thereof.

6. The system of claim 4, wherein the electronic layer is fabricated on a substrate, wherein a conductive trace is in a first ring around the at least one active electrode, wherein the conductive trace in the first ring around the at least one active electrode does not contact the at least one active electrode, wherein a soldermask, a printed ink, or a non-conductive material is printed, deposited, or adhered on the substrate in a second ring around the at least one active electrode, wherein the second ring around the at least one active electrode is inside the first ring around the at least one active electrode, wherein the first ring around the at least one active electrode does not contact the second ring around the at least one active electrode, wherein an ionophore polymer coating is applied to the at least one active electrode via liquid deposition such that the ionophore polymer coating completely covers the at least one active electrode and is contained within the second ring formed by the soldermask, the printed ink, or the non-conductive material, and wherein the non-conductive material is a different material than the substrate.

7. The system of claim 4, wherein the electronic layer is fabricated on a substrate, wherein the substrate includes a well, wherein a conductive trace is in a ring around the well, wherein the conductive trace does not contact the well, wherein the at least one active electrode is within the well, and wherein an ionophore polymer coating is applied to the at least one active electrode via liquid deposition such that the ionophore polymer coating completely covers the at least one active electrode and the ionophore polymer coating is contained within the well on the substrate.

8. The system of claim 1, wherein the apparatus wirelessly transmits the at least one output datum to the at least one remote transceiver device.

9. The system of claim 8, wherein the apparatus wirelessly transmits the at least one output datum via Bluetooth, radiofrequency, zigbee, wi-fi, or near field communication.

10. The system of claim 1, wherein the apparatus continuously monitors the at least one sweat biomarker.

11. The system of claim 1, wherein the input data further includes gender, fitness or conditioning level, age, and a maximum rate of oxygen consumption for the human ($VO_2$max).

12. The system of claim 1, wherein the two-way communication further comprises commands, electrode calibration, microcontroller software updates, new or updated algorithms, new or updated modifying variables for algorithms, microcontroller health properties, error codes, electrode maintenance or malfunction, or a combination thereof.

13. The system of claim 1, wherein the input data is generated in the remote transceiver device by integrated applications.

14. A system for continuously analyzing sweat from a human in real-time and transmitting and storing sweat data from the human comprising:

an apparatus for sensing and analyzing sweat, wherein the apparatus includes an electronic layer comprising at least one electrochemical sensor, a microcontroller, and a transceiver antenna coil;

at least one remote transceiver device; and at least one remote computer server;

wherein the apparatus continuously analyzes at least one sweat biomarker in real-time, calculates at least one output datum of the at least one sweat biomarker using at least one algorithm, and transmits the at least one output datum to the at least one remote transceiver device;

wherein the at least one algorithm calculates the at least one output datum using an estimated body surface area of a human and input data, wherein the input data includes at least a height and a weight of the human, a maximum rate of oxygen consumption for the human ($VO_2$max), and a body mass of the human, and wherein the height and the weight of the human are used to estimate the estimated body surface area of the human;

wherein the at least one remote transceiver device transmits the at least one output datum to the at least one remote computer server or at least one remote computing device or database for storage;

wherein the apparatus and the at least one remote transceiver device have real-time or near-real-time two-way communication;

wherein the electrochemical sensor has at least one reference electrode and at least one active electrode;

wherein the at least one active electrode has an ionophore polymer coating;

wherein the apparatus is flexible and further includes:
a macrofluidic, double-sided adhesive layer;
a microfluidic management layer; and
a vapor porous, top protective layer;

wherein the macrofluidic, double-sided adhesive layer is intimately adhered to an exterior layer of human skin;

wherein the microfluidic management layer is positioned between the macrofluidic, double-sided adhesive layer and the electronic layer;

wherein the microfluidic management layer circumferentially surrounds the at least one electrochemical sensor of the electronic layer;

wherein the at least one electrochemical sensor of the electronic layer is facing the exterior layer of human skin;

wherein the electronic layer is intimately adhered to the macrofluidic, double-sided adhesive layer;

wherein the vapor porous, top protective layer is placed on and completely covers the microfluidic management layer and the electronic layer; and wherein the vapor porous, top protective layer is intimately adhered to the macrofluidic, double-sided adhesive layer.

15. A method for analyzing sweat from a human and transmitting and storing sweat data from the human, the method comprising:

providing an apparatus for sensing and analyzing sweat, wherein the apparatus includes an electronic layer comprising at least one electrochemical sensor, a microcontroller, and a transceiver antenna coil; at least one remote transceiver device; and at least one remote computer server;

wherein the at least one remote transceiver device and the apparatus are operable for two-way cross-communication in real-time or near-real-time;

the at least one electrochemical sensor sensing at least one biomarker of the sweat, which creates a voltage;

the microcontroller converting the at least one biomarker of the sweat into at least one output datum using at least one algorithm, wherein the at least one algorithm calculates the at least one output datum using an estimated body surface area of a human and input data, wherein the input data includes at least a height and a weight of the human, and wherein the height and the weight of the human are used to estimate the estimated body surface area of the human;

the at least one remote transceiver device inputting modifying variables into the at least one algorithm via the two-way communication with the apparatus;

the transceiver antenna coil transmitting the at least one output datum to the at least one remote transceiver device via the two-way communication with the apparatus; and the at least one remote transceiver device sharing or transmitting the at least one datum with the at least one remote computer server or at least one remote computing device or database for storage; and wherein the apparatus is flexible and further includes:
a macrofluidic, double-sided adhesive layer;
a microfluidic management layer; and
a vapor porous, top protective layer;

wherein the macrofluidic, double-sided adhesive layer is intimately adhered to an exterior layer of human skin;

wherein the microfluidic management layer is positioned between the macrofluidic, double-sided adhesive layer and the electronic layer;

wherein the microfluidic management layer circumferentially surrounds the at least one electrochemical sensor of the electronic layer;

wherein the at least one electrochemical sensor of the electronic layer is facing the exterior layer of human skin;

wherein the electronic layer is intimately adhered to the macrofluidic, double-sided adhesive layer;

wherein the vapor porous, top protective layer is placed on and completely covers the microfluidic management layer and the electronic layer; and wherein the vapor porous, top protective layer is intimately adhered to the macrofluidic, double-sided adhesive layer.

16. The method of claim 15, wherein the at least one biomarker of the sweat includes small molecules, proteins, metabolites, and/or electrolytes.

17. The method of claim 15, wherein the at least one output datum includes but is not limited to concentrations, such as molarity, osmolarity, and osmolality, and/or descriptive statistics, such as averages, ratios, and trends, all of which may be categorized based on a sub-range within a larger physiological range of the at least one biomarker.

18. The method of claim 15, wherein the at least one output datum is transmitted from the apparatus to a remote computer device through wireless network communication by the transceiver antenna of the apparatus.

19. The method of claim 18, wherein the wireless network communication is via Bluetooth, radiofrequency, zigbee, wi-fi, or near field communication.

20. The method of claim 15, wherein the input data further includes gender, fitness or conditioning level, age, and a maximum rate of oxygen consumption for the human ($VO_2$max).

* * * * *